US012544068B2

(12) United States Patent
Deck et al.

(10) Patent No.: US 12,544,068 B2
(45) Date of Patent: Feb. 10, 2026

(54) LINEAR SURGICAL STAPLER

(71) Applicant: Cilag GmbH International, Zug (CH)

(72) Inventors: Andrew C. Deck, Cincinnati, OH (US); Benjamin A. Bialorucki, Cincinnati, OH (US); Kevin A. Larson, South Lebanon, OH (US); Anthony Nguyen, West Chester, OH (US); Brian D. Schings, Maineville, OH (US); Richard M. Harper, Blue Ash, OH (US); Kevin J. Zylka, Mason, OH (US); Caterina E. Esposito, Cambridge, MA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/500,398

(22) Filed: Nov. 2, 2023

(65) Prior Publication Data

US 2024/0058002 A1 Feb. 22, 2024

Related U.S. Application Data

(63) Continuation-in-part of application No. 18/316,635, filed on May 12, 2023.

(Continued)

(51) Int. Cl.

*A61B 17/00* (2006.01)

*A61B 17/072* (2006.01)

(52) U.S. Cl.

CPC .................. *A61B 17/07207* (2013.01); *A61B 2017/07271* (2013.01)

(58) Field of Classification Search

CPC ........ A61B 17/115; A61B 2017/00367; A61B 17/072; A61B 17/07207;

(Continued)

(56) References Cited

U.S. PATENT DOCUMENTS 2,066,157 A 12/1936 Pankonin
2,083,227 A 6/1937 Drypolcher (Continued)

FOREIGN PATENT DOCUMENTS

CN 102973300 A 3/2013
CN 104490437 A 4/2015

(Continued)

OTHER PUBLICATIONS

International Search Report and Written Opinion dated Nov. 3, 2023, for International Application No. PCT/IB2023/056026, 27 pages.

(Continued)

*Primary Examiner* — Jacob A Smith

(74) *Attorney, Agent, or Firm* — FBT Gibbons LLP

(57) ABSTRACT

An apparatus includes first and second elongate members having first and second stapling surfaces and being configured to releasably couple together. A clamp member is movable from a first position to a second position to approximate the stapling surfaces for clamping tissue. A latch member is transitionable from an unlatched state to a latched state to releasably retain the clamp member in the second position. A firing assembly is actuatable from a home position to fire staples into the clamped tissue. The latch member is transitionable from the unlatched state to the latched state when the clamp member is in the second position while the firing assembly is in the home position. The latch member is inhibited from transitioning from the unlatched state to the latched state when the clamp member is in the second position while the firing assembly is displaced from the home position.

20 Claims, 35 Drawing Sheets

Related U.S. Application Data

(60) Provisional application No. 63/423,300, filed on Nov. 7, 2022, provisional application No. 63/352,093, filed on Jun. 14, 2022.

(58) Field of Classification Search
CPC A61B 2017/07271; A61B 2017/07257; A61B 17/068
USPC ....................................................... 227/175.2
See application file for complete search history.

(56) References Cited

U.S. PATENT DOCUMENTS

| | | | |
|---|---|---|---|
| 2,311,412 | A | 2/1943 | Pankonin |
| 2,469,984 | A | 5/1949 | Pankonin |
| 2,939,146 | A | 6/1960 | Abrams |
| 2,946,059 | A | 7/1960 | Wandel |
| 4,047,654 | A | 9/1977 | Alvarado |
| 4,180,196 | A | 12/1979 | Hueil et al. |
| 4,312,363 | A | 1/1982 | Rothfuss et al. |
| 4,354,628 | A | 10/1982 | Green |
| 4,453,661 | A | 6/1984 | Genyk et al. |
| 4,506,819 | A | 3/1985 | Rand |
| 4,520,817 | A | 6/1985 | Green |
| 4,522,327 | A | 6/1985 | Korthoff et al. |
| 4,580,712 | A | 4/1986 | Green |
| 4,608,981 | A | 9/1986 | Rothfuss et al. |
| 4,878,608 | A | 11/1989 | Mitsuhashi |
| 4,930,674 | A | 6/1990 | Barak |
| 4,984,729 | A | 1/1991 | Balma |
| 4,991,764 | A | 2/1991 | Mericle |
| 5,071,052 | A | 12/1991 | Rodak et al. |
| 5,074,454 | A | 12/1991 | Peters |
| 5,137,198 | A | 8/1992 | Nobis et al. |
| 5,141,144 | A | 8/1992 | Foslien |
| 5,180,092 | A | 1/1993 | Crainich |
| 5,183,196 | A | 2/1993 | Miyashita |
| 5,190,203 | A | 3/1993 | Rodak |
| 5,312,023 | A | 5/1994 | Green et al. |
| 5,337,937 | A | 8/1994 | Remiszewski et al. |
| 5,389,098 | A | 2/1995 | Tsuruta et al. |
| 5,395,034 | A | 3/1995 | Allen et al. |
| 5,445,304 | A | 8/1995 | Plyley et al. |
| 5,452,837 | A | 9/1995 | Williamson, IV et al. |
| 5,465,894 | A | 11/1995 | Clark et al. |
| 5,489,058 | A | 2/1996 | Plyley et al. |
| 5,533,521 | A | 7/1996 | Granger |
| 5,551,622 | A | 9/1996 | Yoon |
| 5,571,090 | A | 11/1996 | Sherts |
| 5,636,779 | A | 6/1997 | Palmer |
| 5,749,893 | A | 5/1998 | Vidal et al. |
| 5,792,135 | A | 8/1998 | Madhani et al. |
| 5,792,165 | A | 8/1998 | Klieman et al. |
| 5,817,084 | A | 10/1998 | Jensen |
| 5,878,193 | A | 3/1999 | Wang et al. |
| 5,893,506 | A | 4/1999 | Powell |
| 5,988,479 | A | 11/1999 | Palmer |
| 6,152,347 | A | 11/2000 | Wilson et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 7,032,799 | B2 | 4/2006 | Viola et al. |
| 7,296,722 | B2 | 11/2007 | Ivanko |
| 7,334,717 | B2 | 2/2008 | Rethy et al. |
| 7,524,320 | B2 | 4/2009 | Tierney et al. |
| 7,568,604 | B2 | 8/2009 | Ehrenfels et al. |
| 7,691,098 | B2 | 4/2010 | Wallace et al. |
| 7,806,891 | B2 | 10/2010 | Nowlin et al. |
| 7,891,531 | B1 | 2/2011 | Ward |
| 7,905,381 | B2 | 3/2011 | Baxter, III et al. |
| 7,954,686 | B2 | 6/2011 | Baxter, III et al. |
| 8,348,129 | B2 | 1/2013 | Bedi et al. |
| 8,365,971 | B1 | 2/2013 | Knodel |
| 8,479,969 | B2 | 7/2013 | Shelton, IV |
| 8,523,041 | B2 | 9/2013 | Ishitsuki et al. |
| 8,561,870 | B2 | 10/2013 | Baxter, III et al. |
| 8,573,461 | B2 | 11/2013 | Shelton, IV et al. |
| 8,573,465 | B2 | 11/2013 | Shelton, IV |
| 8,602,288 | B2 | 12/2013 | Shelton, IV et al. |
| 8,616,431 | B2 | 12/2013 | Timm et al. |
| 8,783,541 | B2 | 7/2014 | Shelton, IV et al. |
| 8,789,740 | B2 | 7/2014 | Baxter, III et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 8,998,061 | B2 | 4/2015 | Williams et al. |
| 9,155,537 | B2 | 10/2015 | Katre et al. |
| 9,161,807 | B2 | 10/2015 | Garrison |
| 9,237,891 | B2 | 1/2016 | Shelton, IV et al. |
| 9,301,759 | B2 | 4/2016 | Spivey et al. |
| 9,402,629 | B2 | 8/2016 | Ehrenfels et al. |
| 9,451,959 | B2 | 9/2016 | Patankar et al. |
| 9,539,007 | B2 | 1/2017 | Dhakad et al. |
| 9,724,095 | B2 | 8/2017 | Gupta et al. |
| 9,987,007 | B2 | 6/2018 | Kapadia |
| 10,092,292 | B2 | 10/2018 | Boudreaux et al. |
| 10,512,461 | B2 | 12/2019 | Gupta et al. |
| 10,631,866 | B2 | 4/2020 | Laurent et al. |
| 10,667,818 | B2 | 6/2020 | McLain et al. |
| 10,687,819 | B2 | 6/2020 | Stokes et al. |
| 10,874,398 | B2 | 12/2020 | Baxter, III et al. |
| 10,898,187 | B2 | 1/2021 | Deck et al. |
| 10,898,197 | B2 | 1/2021 | Baxter, III et al. |
| 10,905,419 | B2 | 2/2021 | Schings et al. |
| 10,932,781 | B2 | 3/2021 | Jones et al. |
| 11,033,266 | B2 | 6/2021 | Jones et al. |
| 11,045,193 | B2 | 6/2021 | Schings et al. |
| 11,058,421 | B2 | 7/2021 | Shelton, IV et al. |
| 11,219,454 | B2 | 1/2022 | Schings et al. |
| 11,224,425 | B2 | 1/2022 | Schings et al. |
| 11,229,433 | B2 | 1/2022 | Schings et al. |
| 11,278,285 | B2 | 3/2022 | Deck et al. |
| 11,596,406 | B2 | 3/2023 | Huitema et al. |
| 11,755,329 | B2 | 9/2023 | Oshiyama et al. |
| 2002/0005427 | A1 | 1/2002 | Aoki |
| 2002/0188316 | A1 | 12/2002 | Dingler |
| 2003/0178465 | A1 | 9/2003 | Bilotti et al. |
| 2004/0267311 | A1 | 12/2004 | Viola et al. |
| 2005/0222616 | A1 | 10/2005 | Rethy et al. |
| 2006/0231583 | A1 | 10/2006 | Kumayama |
| 2008/0142565 | A1 | 6/2008 | Ehrenfels et al. |
| 2008/0167680 | A1 | 7/2008 | Voegele et al. |
| 2008/0188844 | A1 | 8/2008 | McGreevy et al. |
| 2009/0078739 | A1 | 3/2009 | Viola |
| 2009/0209986 | A1 | 8/2009 | Stewart et al. |
| 2009/0302093 | A1 | 12/2009 | Kasvikis |
| 2009/0308907 | A1 | 12/2009 | Nalagatla et al. |
| 2009/0308909 | A1 | 12/2009 | Nalagatla et al. |
| 2010/0072253 | A1 | 3/2010 | Baxter, III et al. |
| 2010/0213241 | A1 | 8/2010 | Bedi |
| 2010/0282820 | A1 | 11/2010 | Kasvikis |
| 2010/0288815 | A1 | 11/2010 | Maemori |
| 2011/0084115 | A1 | 4/2011 | Bedi et al. |
| 2011/0087276 | A1 | 4/2011 | Bedi et al. |
| 2011/0226837 | A1 | 9/2011 | Baxter, III et al. |
| 2011/0257679 | A1 | 10/2011 | Ishitsuki et al. |
| 2011/0278343 | A1 | 11/2011 | Knodel et al. |
| 2011/0290851 | A1 | 12/2011 | Shelton, IV |
| 2012/0024936 | A1 | 2/2012 | Baxter, III et al. |
| 2012/0074198 | A1 | 3/2012 | Huitema et al. |
| 2012/0248169 | A1 | 10/2012 | Widenhouse et al. |
| 2012/0255986 | A1 | 10/2012 | Petty et al. |
| 2012/0312858 | A1 | 12/2012 | Patankar et al. |
| 2012/0312859 | A1 | 12/2012 | Gupta et al. |
| 2013/0037595 | A1 | 2/2013 | Gupta et al. |
| 2013/0037597 | A1 | 2/2013 | Katre et al. |
| 2013/0140343 | A1 | 6/2013 | Knodel |
| 2013/0306703 | A1 | 11/2013 | Ehrenfels et al. |
| 2014/0200580 | A1 | 7/2014 | Joseph et al. |
| 2014/0239037 | A1 | 8/2014 | Boudreaux et al. |
| 2014/0353357 | A1 | 12/2014 | Agarwal et al. |
| 2015/0018875 | A1 | 1/2015 | Knodel |
| 2015/0034695 | A1 | 2/2015 | Kapadia |
| 2015/0066022 | A1 | 3/2015 | Shelton, IV et al. |

(56) References Cited

U.S. PATENT DOCUMENTS

| | | | |
|---|---|---|---|
| 2015/0282866 A1 | 10/2015 | Rothweiler et al. | |
| 2015/0327855 A1 | 11/2015 | Katre | |
| 2016/0106426 A1 | 4/2016 | Shelton, IV et al. | |
| 2016/0135811 A1 | 5/2016 | Gupta et al. | |
| 2016/0199084 A1 | 7/2016 | Takei | |
| 2016/0213377 A1 | 7/2016 | Shankarsetty et al. | |
| 2016/0249920 A1 | 9/2016 | Gupta et al. | |
| 2016/0262756 A1 | 9/2016 | Patankar et al. | |
| 2016/0310136 A1 | 10/2016 | Gupta et al. | |
| 2016/0338701 A1 | 11/2016 | Patankar et al. | |
| 2016/0338702 A1 | 11/2016 | Ehrenfels et al. | |
| 2017/0079652 A1 | 3/2017 | Dhakad et al. | |
| 2017/0095251 A1 | 4/2017 | Thompson et al. | |
| 2017/0143335 A1 | 5/2017 | Gupta et al. | |
| 2017/0143336 A1 | 5/2017 | Shah et al. | |
| 2017/0325811 A1 | 11/2017 | Gupta et al. | |
| 2018/0015767 A1 | 1/2018 | Kim | |
| 2018/0221102 A1 | 8/2018 | Wang et al. | |
| 2018/0296213 A1 | 10/2018 | Strobl | |
| 2018/0317915 A1 | 11/2018 | McDonald, II | |
| 2020/0046350 A1 | 2/2020 | Deck et al. | |
| 2020/0223045 A1 | 7/2020 | Young et al. | |
| 2020/0405298 A1 | 12/2020 | Ding et al. | |
| 2021/0369270 A1 | 12/2021 | Schings | |
| 2021/0369272 A1 | 12/2021 | Schings | |
| 2022/0142641 A1 | 5/2022 | Wang | |
| 2022/0183684 A1 * | 6/2022 | Schings | A61B 17/07207 |
| 2022/0225987 A1 | 7/2022 | Deck et al. | |
| 2023/0099430 A1 | 3/2023 | Schings et al. | |
| 2023/0397911 A1 | 12/2023 | Deck et al. | |
| 2024/0058002 A1 | 2/2024 | Deck et al. | |

FOREIGN PATENT DOCUMENTS

| | | | | |
|---|---|---|---|---|
| CN | 104739472 A | 7/2015 | | |
| CN | 106037848 A | 10/2016 | | |
| EP | 0061466 A1 | 10/1982 | | |
| EP | 0178941 B1 | 4/1986 | | |
| EP | 0677273 B1 | 10/1995 | | |
| EP | 1702567 B1 | 9/2006 | | |
| EP | 2165652 A1 | 3/2010 | | |
| EP | 2532312 B1 | 12/2012 | | |
| EP | 2804541 A2 | 11/2014 | | |
| EP | 2944270 A1 | 11/2015 | | |
| EP | 3065649 A1 | 9/2016 | | |
| EP | 2741685 B1 | 1/2017 | | |
| EP | 3155988 A1 | 4/2017 | | |
| EP | 2804541 B1 | 10/2017 | | |
| EP | 3520710 A1 | 8/2019 | | |
| EP | 3610801 A2 * | 2/2020 | A61B 17/07207 | |
| EP | 3636166 A2 | 4/2020 | | |
| EP | 3639757 A2 | 4/2020 | | |
| JP | H06-26812 U | 4/1994 | | |
| JP | H10-24742 A | 1/1998 | | |
| JP | 2004-140395 A | 5/2004 | | |
| WO | WO 2012/072138 A1 | 6/2012 | | |
| WO | WO 2013/109445 A2 | 7/2013 | | |
| WO | WO 2017/056028 A1 | 4/2017 | | |
| WO | WO 2018/044669 A1 | 3/2018 | | |

OTHER PUBLICATIONS

Design U.S. Appl. No. 29/842,580, entitled "Staple Cartridge for a Linear Surgical Stapler," filed Jun. 14, 2022.

Design U.S. Appl. No. 29/842,581, entitled "Linear Surgical Stapler," filed Jun. 14, 2022.

Non-Provisional U.S. Appl. No. 18/316,635, entitled "Linear Surgical Stapler," filed May 12, 2023.

International Preliminary Report on Patentability for PCT/IB2023/056026, mailed Dec. 10, 2024, 18 pages.

International Search Report and Written Opinion for PCTIB2024/060815, dated Feb. 13, 2025, 20 pages.

* cited by examiner

LINEAR SURGICAL STAPLER

PRIORITY

This application is a continuation-in-part of U.S. Non-Provisional application. Ser. No. 18/316,635, filed May 12, 2023, entitled "Linear Surgical Stapler," published as U.S. Pub. No. 2023/0397911 on Dec. 14, 2023, which claims the benefit of U.S. Provisional App. No. 63/352,093, filed Jun. 16, 2022, and U.S. Provisional App. No. 63/423,300, filed Nov. 7, 2022, the disclosures of which are incorporated by reference herein in their entireties.

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to releasably couple together and pivot relative to one another to clamp tissue positioned between the two distal jaws when the clamp lever is closed. A firing assembly of the stapler is configured to be actuated to cut the clamped layers and simultaneously drive staples through the tissue on either side of the cut line. After the stapler is fired, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
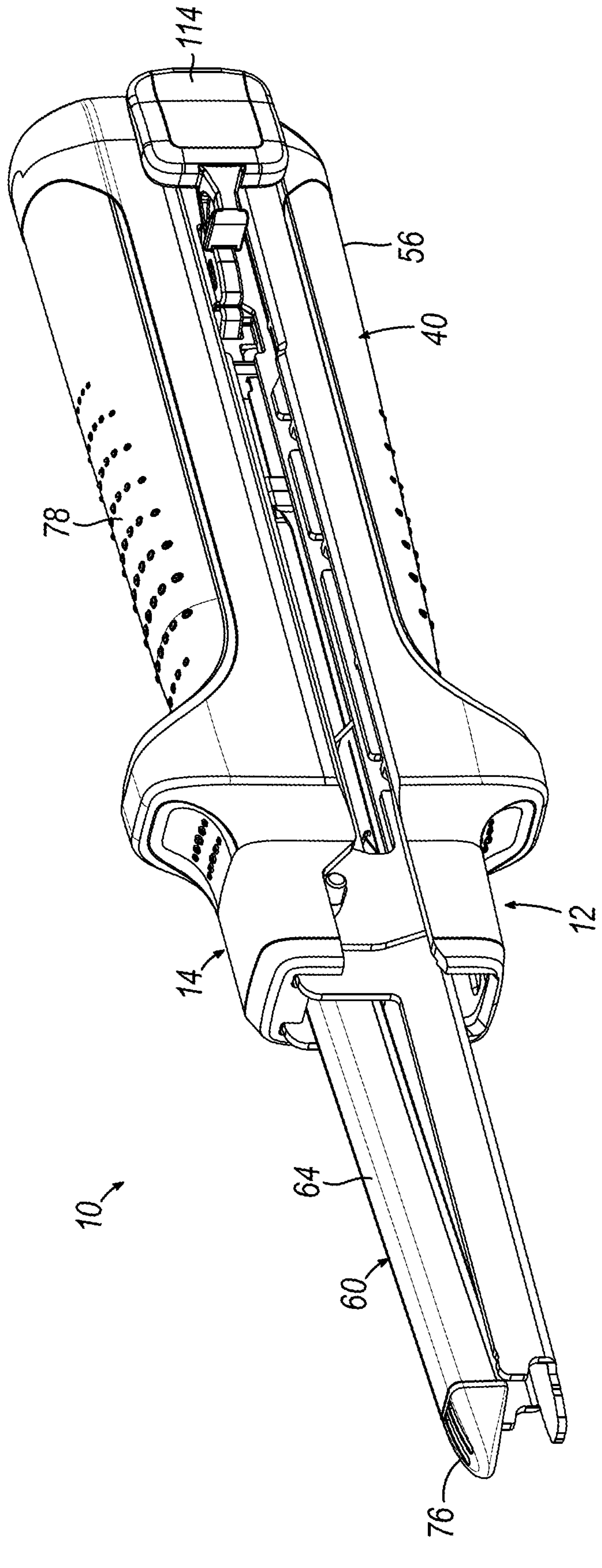
FIG. 1 depicts a perspective view of an illustrative linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms “proximal” and “distal” are defined herein relative to a surgeon, or other operator, grasping a surgical instrument having a distal surgical end effector. The term “proximal” refers to the position of an element arranged closer to the surgeon, and the term “distal” refers to the position of an element arranged closer to the surgical end effector of the surgical instrument and further away from the surgeon. Moreover, to the extent that spatial terms such as “upper,” “lower,” “vertical,” “horizontal,” or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

Furthermore, the terms “about” and “approximately” as used herein in connection with any numerical values or ranges indicate a suitable dimensional tolerance that allows the referenced feature(s) to function for its intended purpose as described herein.

I. Illustrative Linear Surgical Staplers

A. Overview of Linear Surgical Stapler

Figure 2:
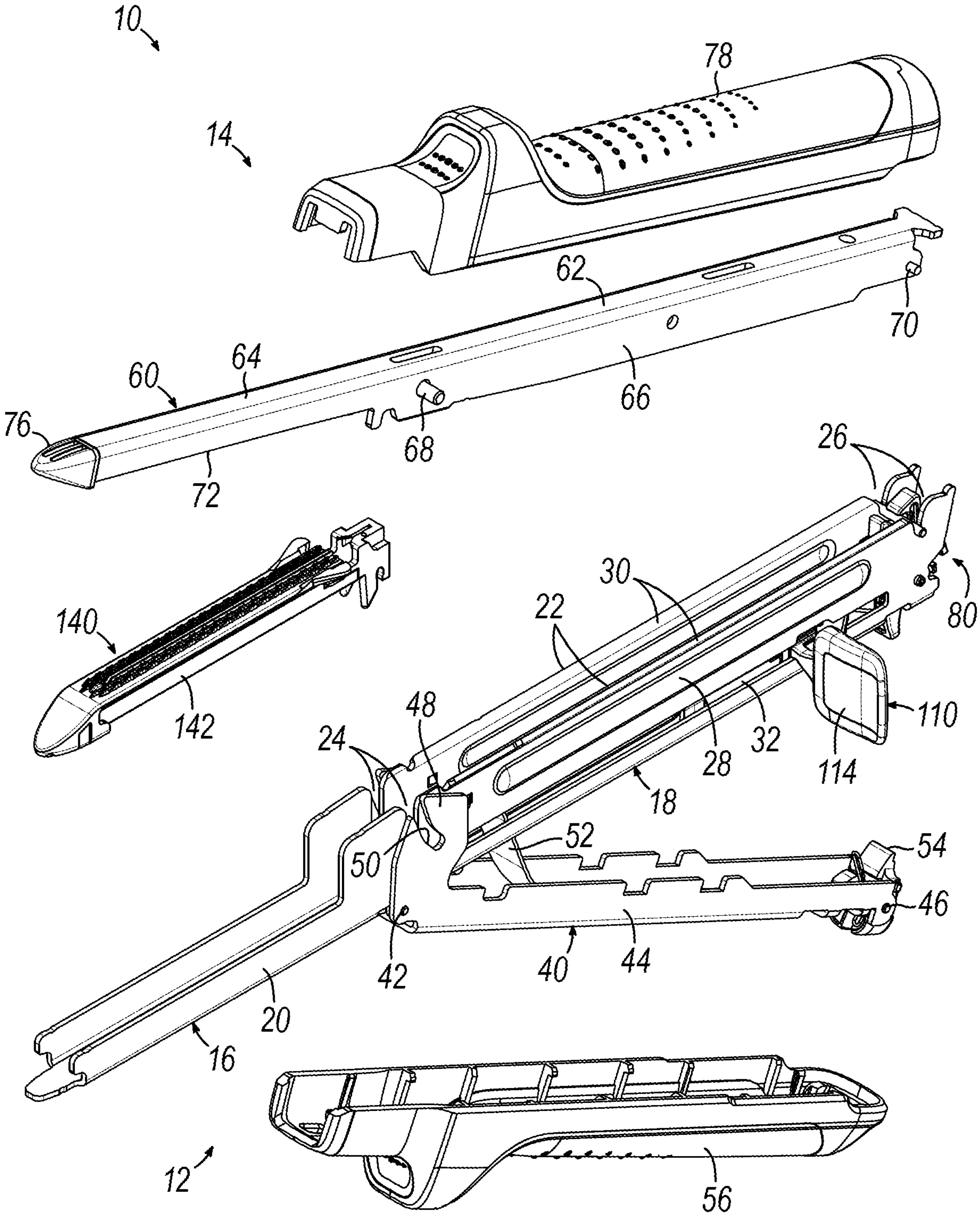
FIG. 2 depicts an exploded perspective view of the linear surgical stapler of FIG. 1, additionally showing a staple cartridge.

FIGS. 1-2 show an illustrative linear surgical stapler (10) (also referred to as a “linear cutter”) suitable for use in a variety of cutting and stapling procedures, such as a gastrointestinal anastomosis procedure. Linear surgical stapler (10) includes a cartridge half (12) (also referred to as a “reload half”) and an anvil half (14) configured to releasably couple together to clamp tissue therebetween for simultaneous cutting and stapling of the clamped tissue.

Cartridge half (12) includes a first elongate member (also referred to as a first elongate body) in the form of an elongate cartridge channel (16) having a proximal frame portion (18) and a distal jaw portion (20). Proximal frame portion (18) slidably retains a firing assembly (110) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness.

An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (110) between proximal and distal positions. Firing assembly (110) is described in greater detail below in connection with FIG. 8.

Distal jaw portion (20) of cartridge channel (16) is configured to releasably receive a staple cartridge (140) (or "reload"). As shown in FIGS. 4 and 9-16, staple cartridge (140) includes a cartridge body (142) having an upper side that defines a first stapling surface in the form of a deck (156) having a plurality of staple openings (166) that house a plurality of staples (168) and corresponding staple drivers (172) (see FIG. 16). Illustrative features of staple cartridge (140) are described in greater detail below in connection with FIGS. 9-16.

Cartridge half (12) further includes a third elongate member and clamp member in the form of a clamp lever (40) (also referred to as a "clamp arm" or "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 19A:
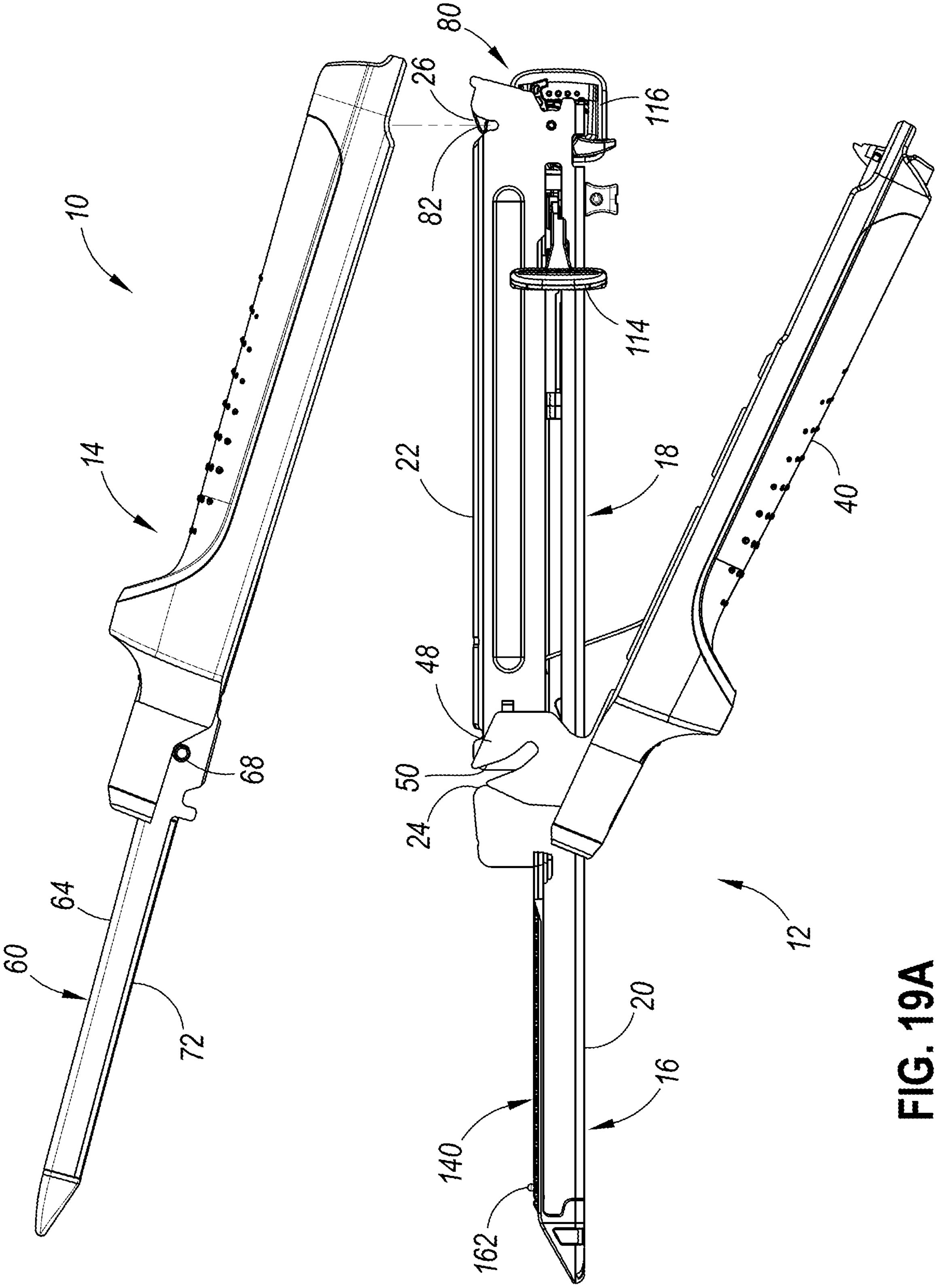
FIG. 19A depicts a side elevational view of the linear surgical stapler of FIG. 1, showing the stapler halves separated from one another with the clamp lever in the open position.
Figure 19B:
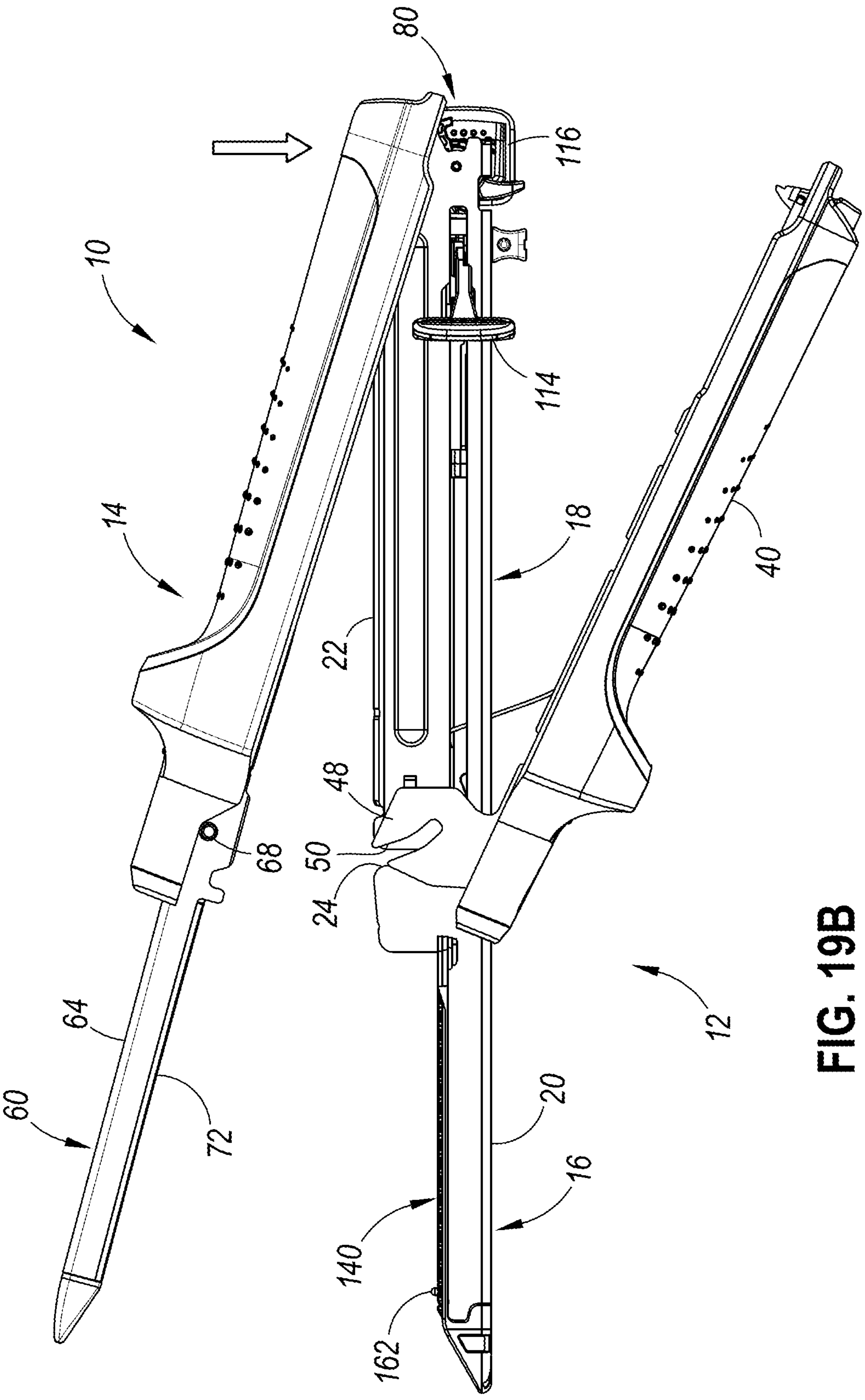
FIG. 19B depicts a side elevational view of the linear surgical stapler of FIG. 1, showing proximal ends of the stapler halves coupled together while the clamp lever is in the open position to provide the stapler in a "hang-open" state.
Figure 19C:
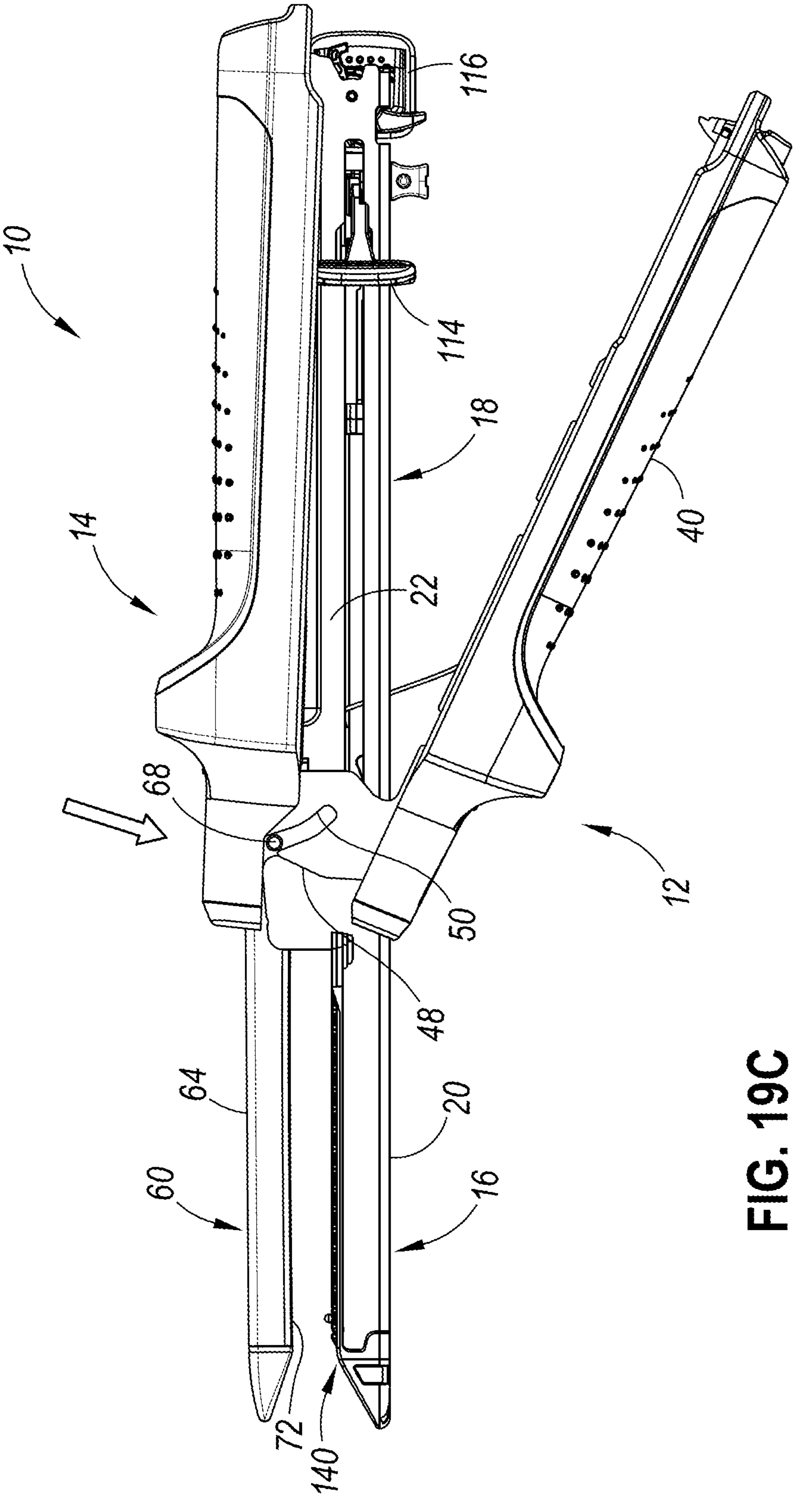
FIG. 19C depicts a side elevational view of the linear surgical stapler of FIG. 1, showing distal portions of the stapler halves having been approximated so that a distal pin of the anvil half is received by clamp lever jaws of the cartridge half.

Clamp lever (40) is operable to pivot relative to cartridge channel (16) between an open position in which proximal end (46) of lever arm (44) is spaced from cartridge channel frame portion (18) as shown in FIGS. 19A-19C described below, and a closed position in which proximal end (46) confronts cartridge channel frame portion (18) as shown in FIG. 9D described below. Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 19C-19D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a leaf spring (52) biases lever arm (44) toward the open position. Accordingly, leaf spring (52) promotes disengagement of clamp lever jaws (48) from anvil half latch pin (68) upon initial advancement of clamp lever (40) from the closed position toward the open position.

As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired. Clamp lever latch member (54) may be further configured in accordance with the teachings of U.S. Pat. No. 11,278,285, entitled "Clamping Assembly for Linear Surgical Stapler," issued Mar. 22, 2022, the disclosure of which is incorporated by reference herein. An illustrative variation of clamp lever latch member (54) is described in greater detail below in connection with FIGS. 20-23.

Anvil half (14) of linear surgical stapler (10) includes a second elongate member (also referred to as a second elongate body) in the form of an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) (also referred to as a pin) extends laterally through the distal ends of anvil channel side flanges (66), and a proximal pivot projection in the form of a proximal pin (70) extends laterally through the proximal ends of anvil channel side flanges (66). Anvil half pins (68, 70) are configured to facilitate coupling of anvil half (14) with cartridge half (12), as described below.

Figure 3:
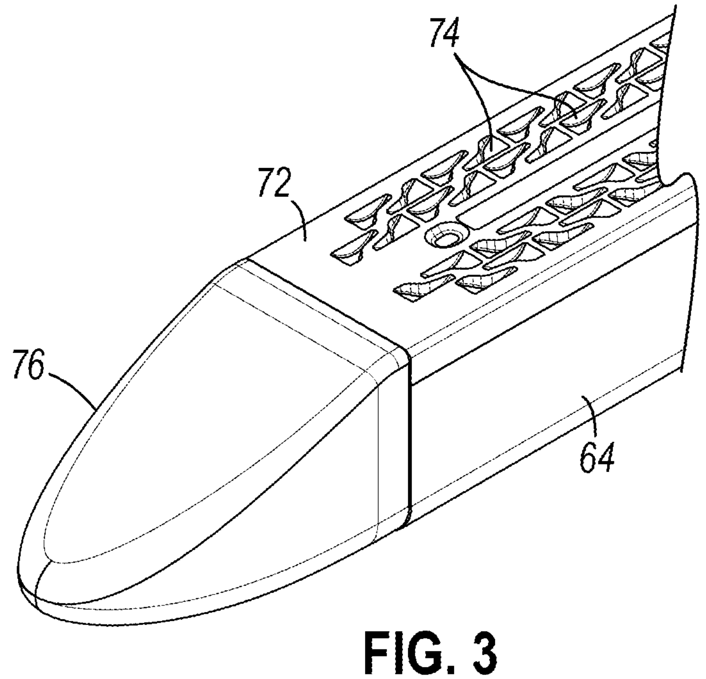
FIG. 3 depicts a perspective view of a distal end portion of the anvil half of the linear surgical stapler of FIG. 1.
Figure 4:
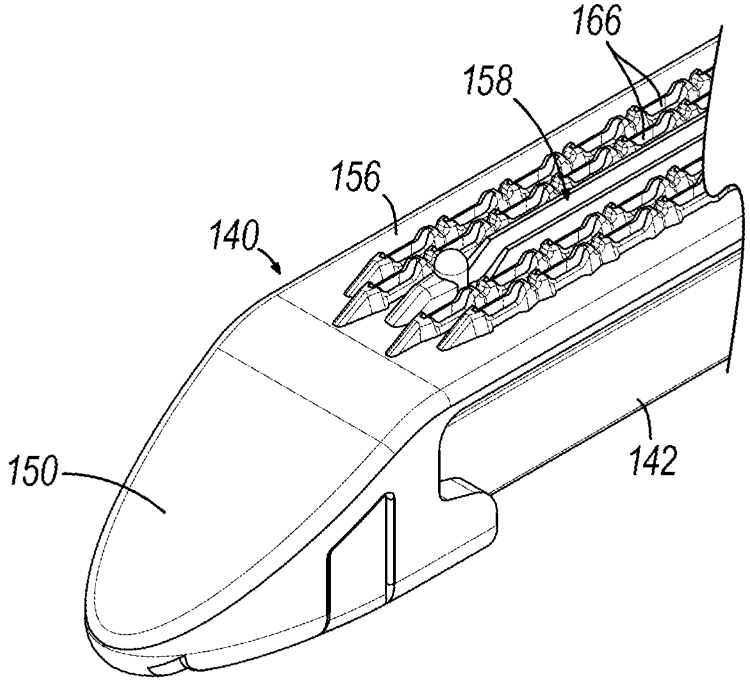
FIG. 4 depicts a perspective view of a distal end portion of the staple cartridge of FIG. 2.

As shown in FIGS. 2 and 3, distal jaw portion (64) of anvil half (14) supports an anvil plate (72) that defines a second stapling surface in the form of an anvil surface having a plurality of staple forming pockets (74) configured to deform legs of staples ejected by staple cartridge (140) when stapler (10) is fired. Staple forming pockets (74) of the present example may be formed via a coining process and are configured to form each staple of staple cartridge (140) with a three-dimensional shape in which the legs of each formed staple are laterally offset from one another so as to provide the formed staple with a non-planar shape, for example as disclosed in U.S. Pat. No. 11,229,433, entitled "Linear Surgical Stapler," issued Jan. 25, 2022, the disclosure of which is incorporated by reference herein. Anvil channel (60), anvil plate (72), and staple forming pockets (74) may be formed in one or more of the manners disclosed in U.S. Pat. Nos. 11,229,433; 11,045,193, entitled "Anvil Assembly for Linear Surgical Stapler," issued Jun. 29, 2021; and/or U.S. Pub. No. 2022/0142641, entitled "System and Method for Forming Pockets in Anvil of Surgical Stapler," published May 12, 2022 and issued as U.S. Pat. No. 12,016,555 on Jun. 25, 2024, the disclosures of which are incorporated by reference herein. For instance, distal jaw portion (64) of anvil half (14) may be pre-formed with a curvature along its length that accommodates deflection of distal jaw portion (64) and anvil plate (72) when stapler halves (12, 14) are clamped together by clamp lever (40). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler, issued Jun. 15, 2021, the disclosure of which is incorporated by reference herein.

As shown in FIG. 2, linear surgical stapler (10) further includes a pair of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) via interaction between pins (68, 70) and one or more tabs, ribs, or other structures that are disposed within an interior of anvil shroud (78) and include an opening, slot, keyhole, or other feature configured to receive a respective one of pins (68, 70). By way of example only, shrouds (56, 78) may be affixed using one or more of the teachings of U.S. Pat. No. 11,278,285, incorporated by reference above. In other versions, shrouds (56, 78) may be coupled with clamp lever (40) and anvil channel (60) in a variety of other suitable manners readily apparent to those of ordinary skill in the art in view of the teachings herein.

As shown best in FIGS. 2 and 5-7, a proximal end of cartridge half (12) includes a retaining assembly (80) configured to releasably retain portions of anvil half (14) and firing assembly (110). Retaining assembly (80) of the present example includes a first movable retaining member in the form of an anvil latch member (82) and a second movable retaining member in the form of a detent member (84). Anvil latch member (82) and detent member (84) are rotatably coupled with a proximal end of cartridge channel (16) via a laterally extending pin (85) arranged proximally of firing slots (32), and members (82, 84) are resiliently biased in opposite rotational directions by a resilient member in the form of a torsion spring (86) positioned between members (82, 84).

Anvil latch member (82) includes a central body (88), a latch finger (90) extending upwardly from central body (88), and a release button (92) extending downwardly from central body (88) though a base wall of proximal frame portion (18) of cartridge channel (16). An upper end of latch finger (90) tapers distally and is configured to releasably capture proximal anvil pin (70) of anvil half (14) with an angled latching surface (94) that overlies proximal anvil pin (70) once captured. Anvil latch member (82) further includes a pin ejection feature in the form of an angled projection (96) extending distally from a base portion of latch finger (90) and which defines an ejection cam ramp (98) that faces proximally toward latch finger (90).

Detent member (84) of proximal retaining assembly (80) includes a generally cylindrical central body (100), a distal finger (102) extending distally from central body (100), and a proximal hook (104) extending proximally from central body (100). Distal finger (102) is configured to releasably engage a proximal end of firing assembly (110) and thereby retain firing assembly (110) in a proximal home position. Proximal hook (104) is configured to overlie and capture an upper tip of clamp lever latch member (54) when clamp lever (40) is fully closed and firing assembly (110) is translated distally from its proximal home position, thereby preventing clamp lever (40) from opening during a firing stroke, for example as described in greater detail in U.S. Pat. No. 11,278,285, incorporated by reference above.

In use, with stapler halves (12, 14) coupled together at their proximal ends such that proximal anvil pin (70) is retained by anvil latch member (82), and with clamp lever (40) in the open position, distal actuation of lower release button (92) causes anvil latch member (82) to rotate about pin (85) such that ejection cam ramp (98) advances proximally to drive proximal anvil pin (70) upwardly out of proximal tapered notches (26) of cartridge channel (16). Cartridge half (12) of the present version further includes a stationary finger grip projection (106) that extends downwardly from a base wall of proximal frame portion (18) of cartridge channel (16) at a location distal to lower release button (92), and is configured to facilitate actuation of release button (92). In particular, a user may apply his or her thumb to a proximal side of release button (92) and one or more fingers to a distal side of finger grip projection (106), and then squeeze release button (92) distally toward stationary finger grip projection (106) to rotate latch finger (90) out of engagement with proximal anvil pin (70) and eject pin (70) upwardly from cartridge channel (16) with ejection cam ramp (98).

Retaining assembly (80) and related components of cartridge half (12) may be further configured and operable in accordance with one or more teachings of U.S. Pat. No. 10,898,187, entitled "Firing System for Linear Surgical Stapler," issued Jan. 26, 2021, the disclosure of which is incorporated by reference herein; and/or U.S. Pat. No. 11,033,266, incorporated by reference above.

Figure 8:
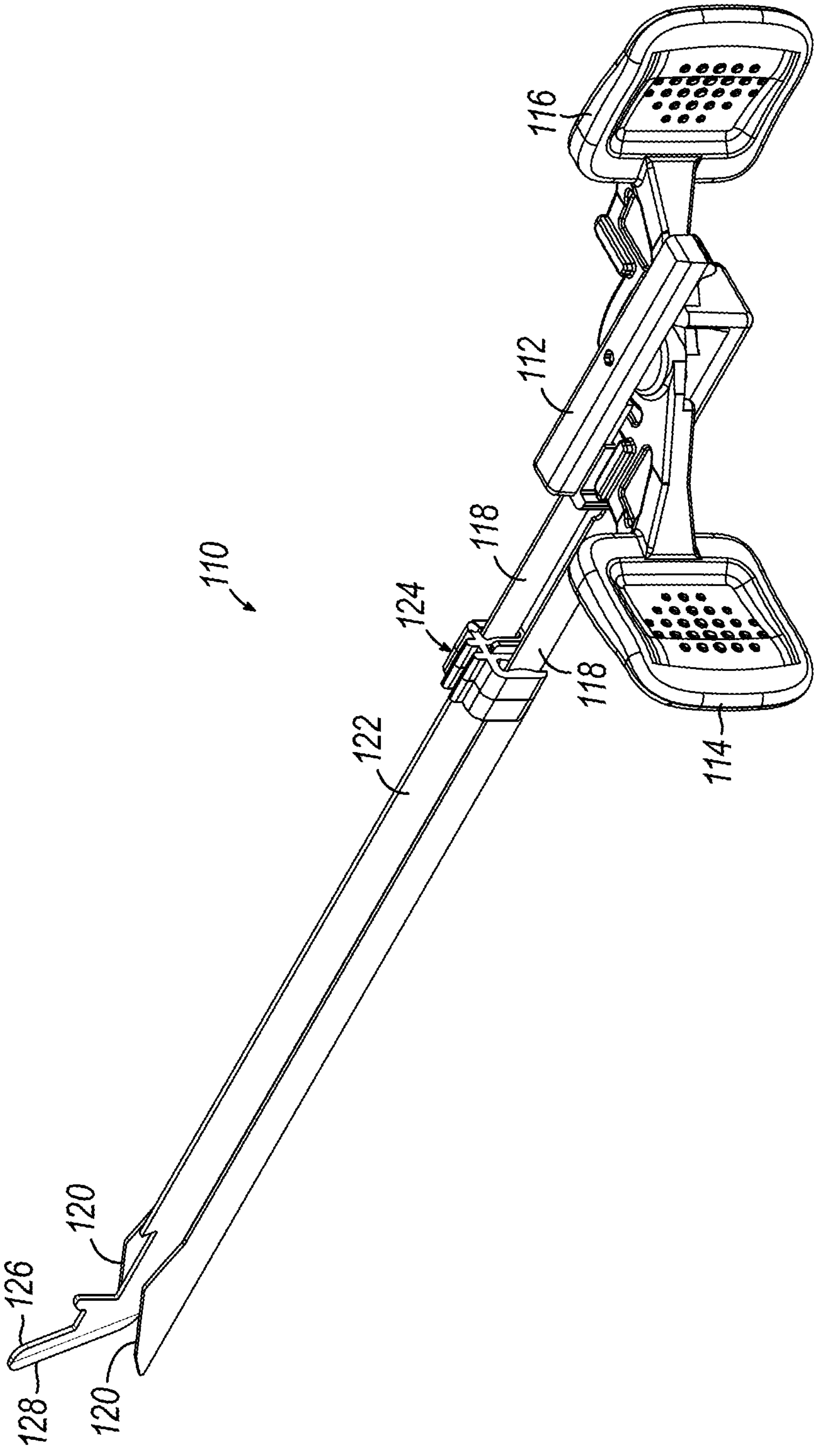
FIG. 8 depicts a perspective view of the firing assembly of FIG. 5.
Figure 9:
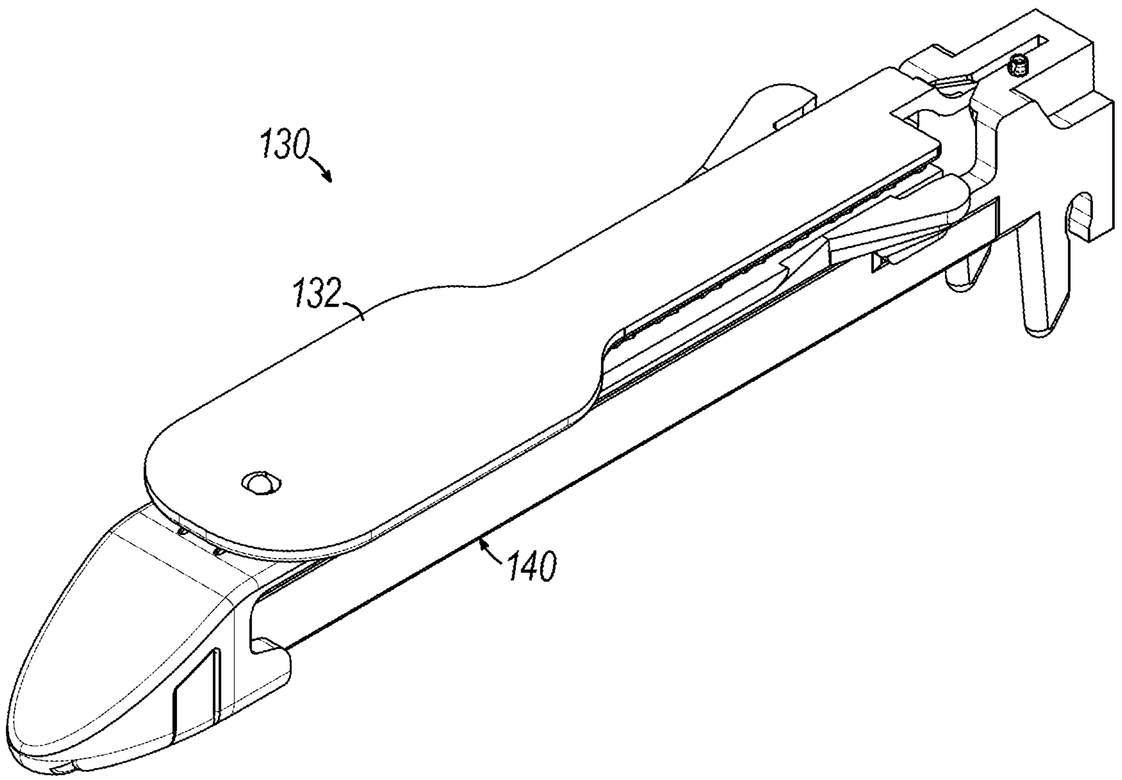
FIG. 9 depicts a perspective view of a staple cartridge assembly that includes the staple cartridge of FIG. 2.
Figure 10:
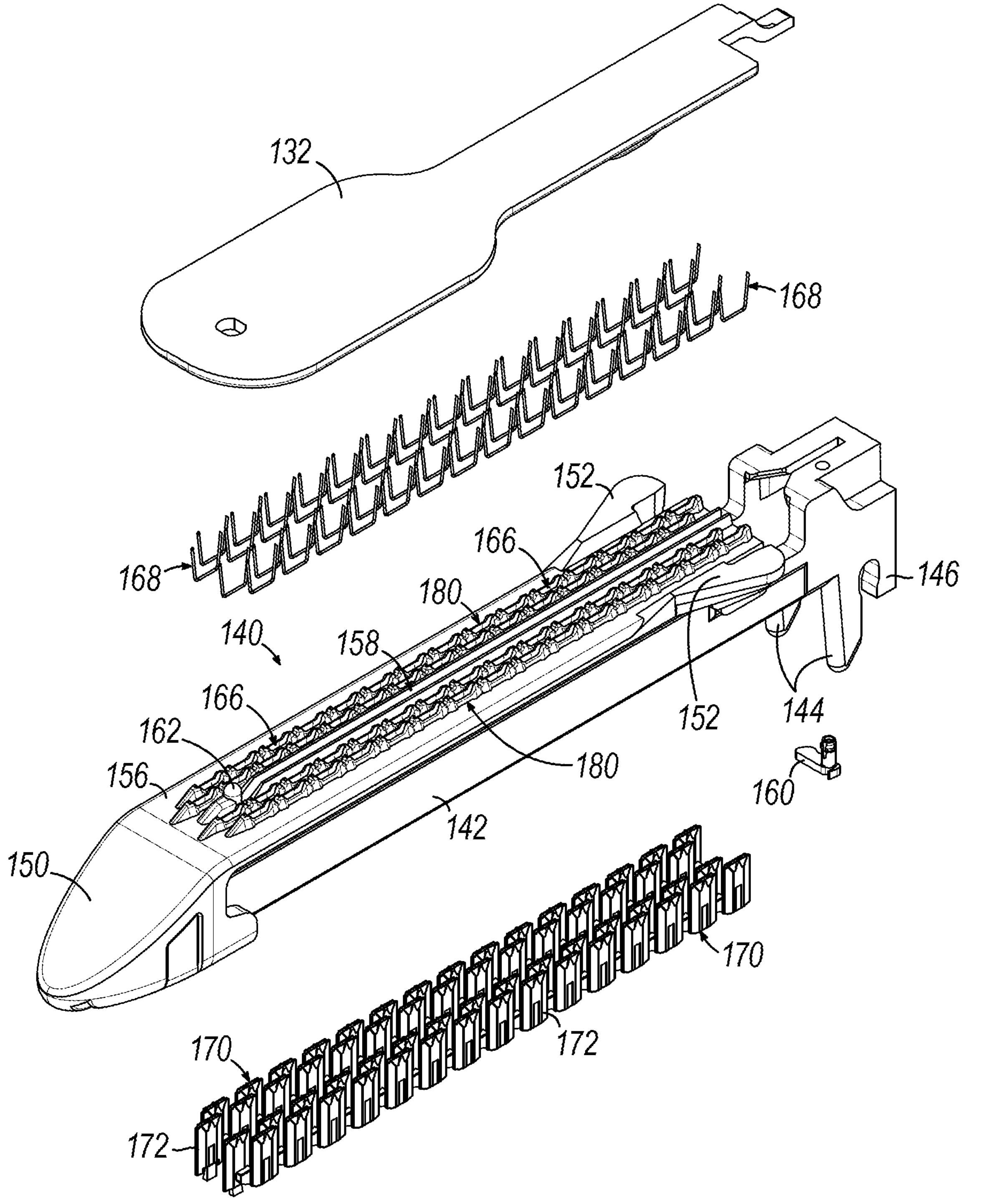
FIG. 10 depicts an exploded perspective view of the staple cartridge assembly of FIG. 9.
Figure 11:
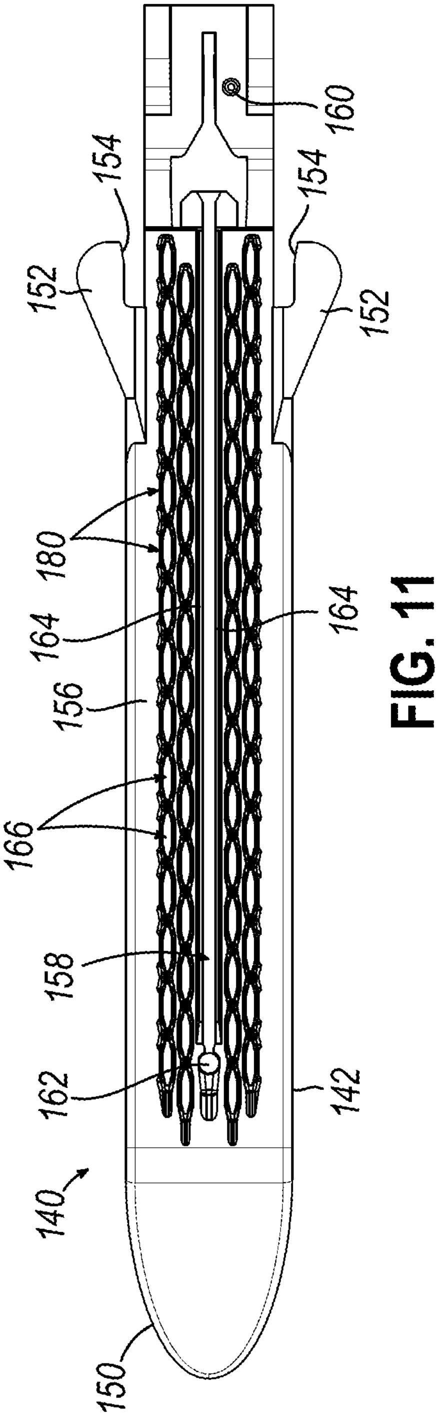
FIG. 11 depicts a top plan view of the staple cartridge of FIG. 9.
Figure 12:
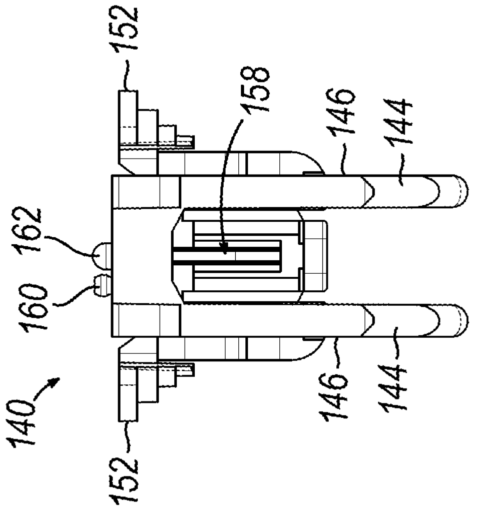
FIG. 12 depicts a rear elevational view of the staple cartridge of FIG. 9.

As shown in FIG. 8, firing assembly (110) of cartridge half (12) includes a slide block (112), a pair of actuators (114, 116) (or "firing knobs") pivotably coupled to slide block (112), and a set of elongate beams (118, 122) extending distally from slide block (112). A pair of side beams (118) are coupled at their proximal ends to a distal end of slide block (112) and terminate distally in a pair of cam ramps (120). Cam ramps (120) are configured to engage the undersides of staple drivers (172) (see FIGS. 10 and 15) housed within staple cartridge (140) and actuate staple drivers (172) upwardly to thereby drive (or "fire") staples from cartridge (130) into tissue clamped between staple cartridge (140) and anvil plate (72). A center beam (122) is coupled with side beams (118) via a bridge member (124) (or "knife block") spaced distally from slide block (112). Center beam (122) terminates distally in a distally angled knife member (126) having a distal cutting edge (128) configured to cut tissue clamped between the distal portions of stapler halves (12, 14).

Each actuator (114, 116) of firing assembly (110) is configured and rotatable relative to slide block (112) between a deployed position and a retracted position such that only one actuator (114, 116) may be deployed at a time, for example as disclosed in U.S. Pat. No. 10,898,187, incorporated by reference above. In the deployed position, an actuator (114, 116) may be driven distally by an operator to actuate firing assembly (110) distally through stapler (10) and thereby simultaneously cut and staple tissue clamped between stapler halves (12, 14).

B. Illustrative Staple Cartridges

FIGS. 9-16 show an illustrative staple cartridge assembly (130) configured for use with linear surgical stapler (10). Staple cartridge assembly (130) includes staple cartridge (140) and a retainer (132) configured to releasably couple with staple cartridge (140) to retain staples (168) in staple cartridge (140) before use.

Figure 20:
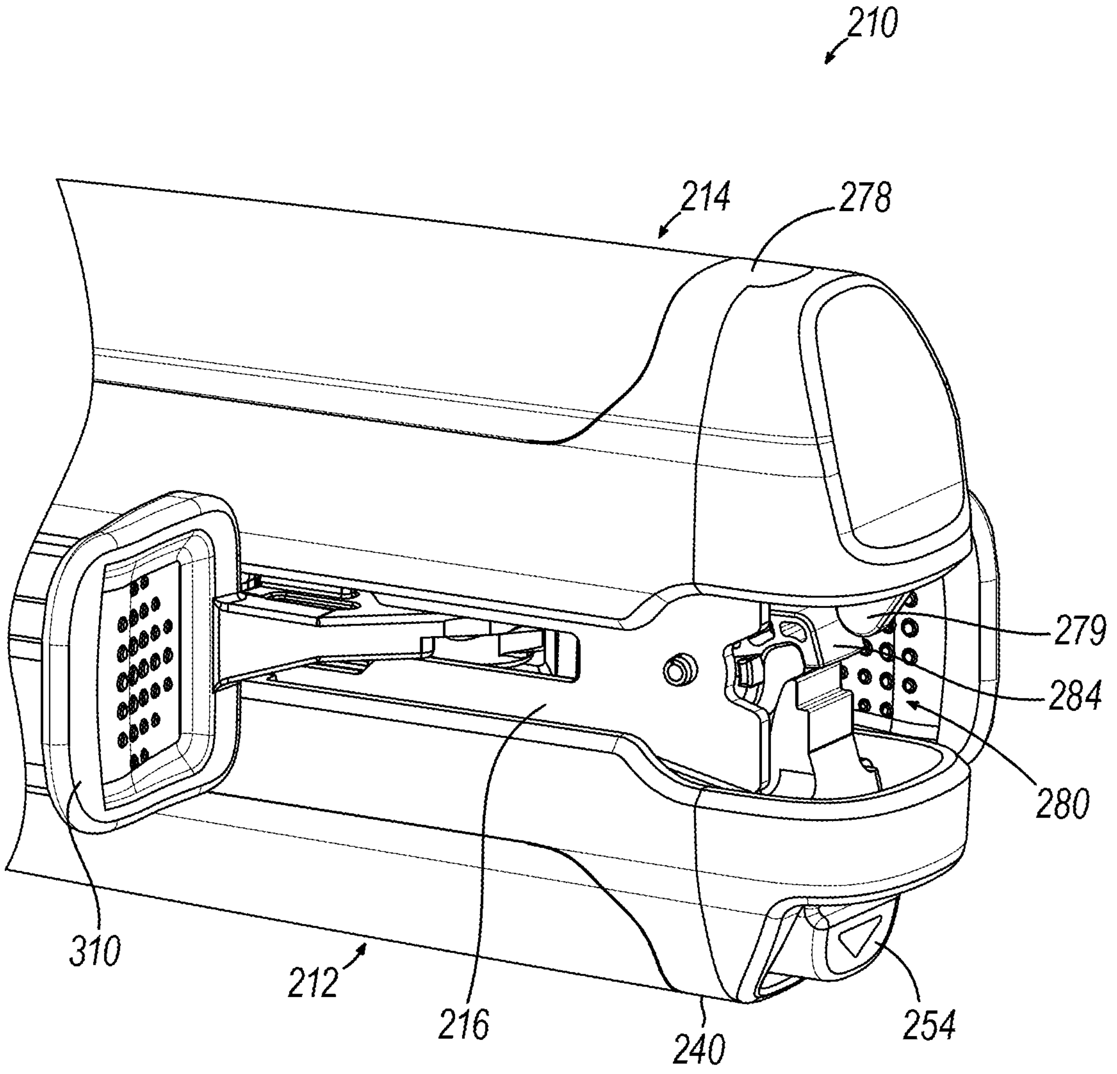
FIG. 20 depicts a perspective view of a proximal portion of another illustrative linear surgical stapler, showing a cartridge half and an anvil half of the stapler coupled together with a clamp lever of the cartridge half in a fully closed position with a latch member of the clamp lever in a latched state.

Staple cartridge (140) includes a cartridge body (142) that extends linearly along a longitudinal axis between a proximal end having a cartridge channel coupling feature in the form of a plurality of downwardly extending coupling legs (144, 146) (also known as "fangs"), and a distal end having a tapered nose (150). Coupling legs (144, 146) are configured to releasably capture clamp lever pivot pin (42) and extend downwardly through corresponding openings formed in a floor of cartridge channel (16) when staple cartridge (140) is seated within distal jaw portion (20) of cartridge channel (16). A pair of wing tabs (152) disposed on the lateral sides of cartridge body (142) near the proximal end are configured to facilitate insertion and removal of staple cartridge (140) relative to distal jaw portion (20). As shown in FIG. 20, an interior side of each wing tab (152) includes a chamfer (154) at its proximal end that serves as a relief feature to provide clearance for the sidewalls of distal jaw portion (20) to facilitate installation and removal of staple cartridge (140) without interference.

An upper side of cartridge body (142) defines a deck (156). An elongate knife slot (158) extends longitudinally through deck (156) along the longitudinal axis of staple cartridge (140) and is configured to slidably receive knife member (126) of firing assembly (110) therethrough in response to distal actuation thereof, described above. A firing lockout bypass feature in the form of a swing tab (160) is rotatably coupled to cartridge body (142) at a proximal end of knife slot (158). Swing tab (160) is configured to rotate between a deployed position in which swing tab (160) extends perpendicularly across the proximal end of knife slot (158), and a retracted position in which swing tab (160) extends parallel to knife slot (158). Swing tab (160) in the deployed position is configured to urge firing assembly (110) from a lockout state toward a firing state in which firing beams (118, 122) may translate distally through staple cartridge (140) to enact stapling and cutting of tissue clamped by stapler (10).

A rigid tissue gap post (162) is secured at a distal end of knife slot (158) and protrudes upwardly away from cartridge deck (156). A rounded upper end of tissue gap post (162) is configured to contact a distal end of anvil plate (72) and thereby define a tissue gap of predetermined size between cartridge deck (156) and anvil plate (72) when stapler halves (12, 14) are clamped together in the manner described above.

A pair of elongate ribs (164) extend along opposing sides of knife slot (158) and project away from deck (156) to define raised surfaces. Elongate ribs (164) terminate at proximal and distal ends of knife slot (158) and are configured to promote enhanced gripping of tissue along knife slot (158), thus stabilizing the tissue during cutting by knife member (126).

Cartridge body (142) of staple cartridge (140) further includes a plurality of staple openings (166) that extend transversely through cartridge body (142) and open to deck (156). In the present example, staple openings (166) are arranged in first and second parallel rows along each side of knife slot (158), such that the staple openings (166) of each row are longitudinally staggered relative to staple openings (166) of the adjacent row. It will be understood that various suitable arrangements and quantities of staple openings (166) may be provided in other versions of staple cartridge (140). Each staple opening (166) is configured to house a respective staple (168) and staple driver (172). As described above, cam ramps (120) of firing assembly (110) are configured to engage the undersides of staple drivers (172) and actuate staple drivers (172) upwardly within staple openings (166) to drive (or "fire") staples (170) from staple openings (166), into tissue, and against anvil plate (72).

Figure 13:
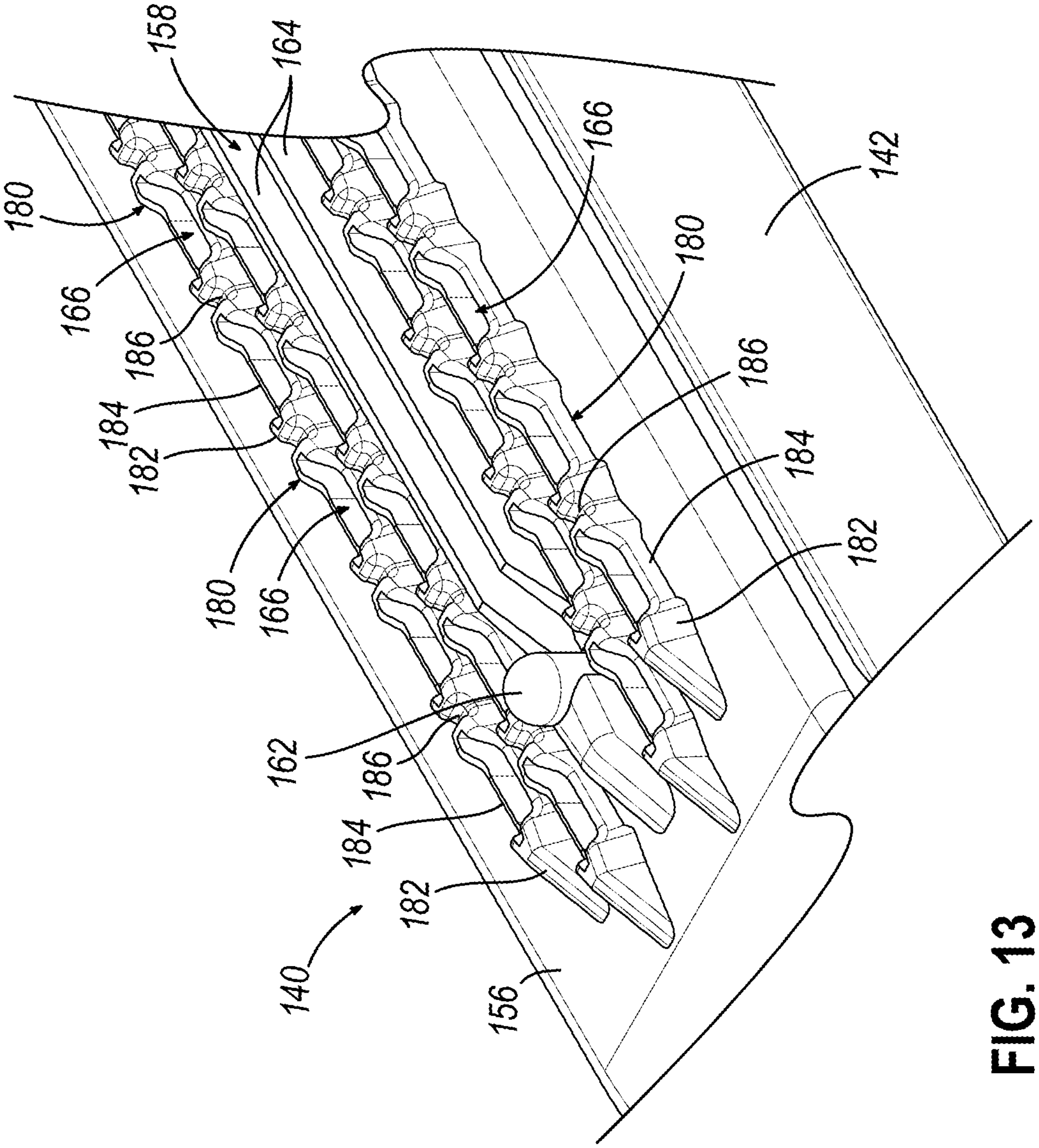
FIG. 13 depicts an enlarged perspective view of a distal portion of the staple cartridge of FIG. 9, showing tissue gripping members formed on a deck of the staple cartridge.
Figure 14:
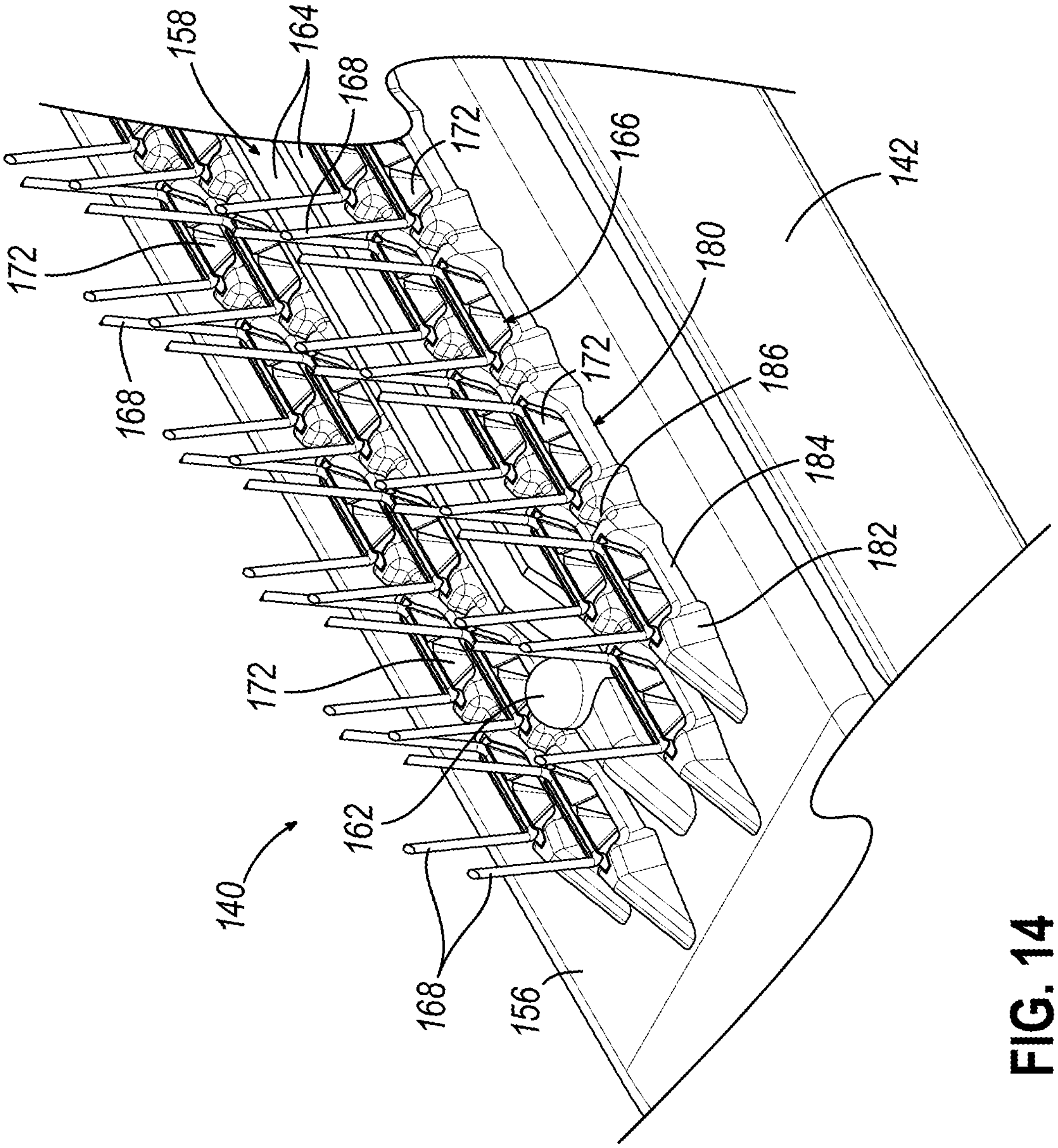
FIG. 14 depicts an enlarged perspective view of a deck portion of the staple cartridge of FIG. 9, showing bridge elements of the tissue gripping members and showing staple drivers and staples of the staple cartridge in an actuated state.

As shown best in FIGS. 13-14, staple cartridge (140) further includes a plurality of tissue gripping members (180) arranged on and projecting upwardly from cartridge deck (156). Tissue gripping members (180) are distributed along a length of deck (156) and are laterally offset from knife slot (158) and elongate ribs (164) to align with and open to a respective one or more staple openings (166). Tissue gripping members (180) are configured to grip and thereby stabilize tissue when deck (156) and anvil plate (72) are clamped together; and, further, optimize tissue compression at the staple locations to facilitate effective stapling and cutting of the tissue. Tissue gripping members (180) of the present version are integrally connected with cartridge body (142).

Each tissue gripping member (180) includes a first end feature (182) that wraps partially around a first end portion of a staple opening (166), and an opposed second end feature (182) that wraps partially around an opposed second end portion of the same staple opening (166). A pair of bridge elements (184) extend between the first and second end features (182) along opposed lateral sides of the staple opening (166) and are recessed relative to the first and second end features (182). Accordingly, each bridge element (184) has a maximum height relative to deck (156) that is less than a maximum height of each of the first and second end features (182). Each pair of bridge elements (184) is configured to cooperate with the respective end features (182) to compress and grip tissue around the respective staple opening (166), and to guide a respective staple driver (172) toward anvil plate (72) without contacting the legs of the respective staple (168) during staple leg formation. Such compression of tissue by end features (182) and bridge elements (184) assists in gripping and stabilizing the tissue, while also minimizing the compression of tissue by staple drivers (172) themselves, which in turn minimizes the user input force required to fire stapler (10). Additionally, at least one end feature (182) associated with each staple opening (166) is integrally connected with an adjacent end feature (182) associated with a longitudinally adjacent staple opening (166), with a recessed region (186) located between each integrally connected pair of end features (182).

Figure 15:
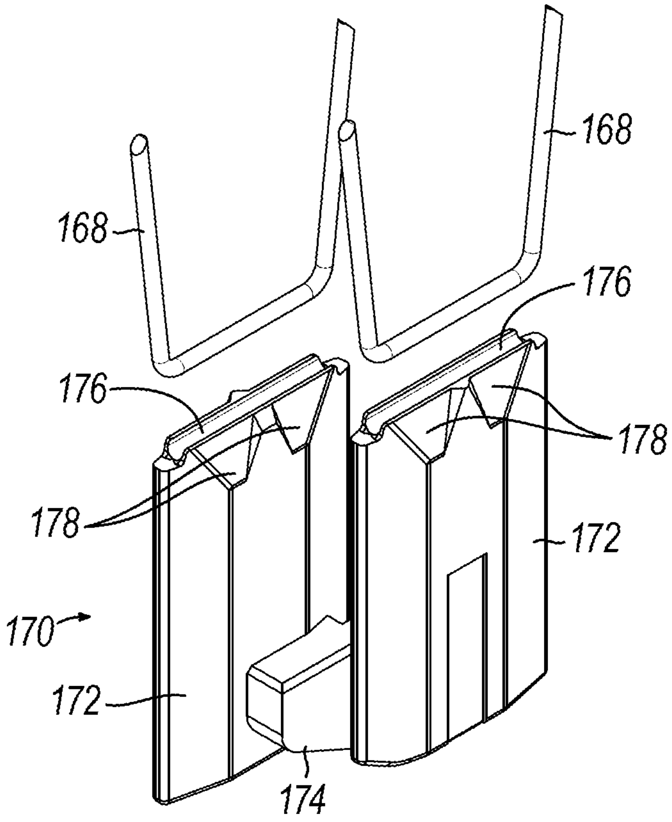
FIG. 15 depicts a perspective view of a staple driver unit and a corresponding pair of staples of the staple cartridge of FIG. 9.
Figure 16:
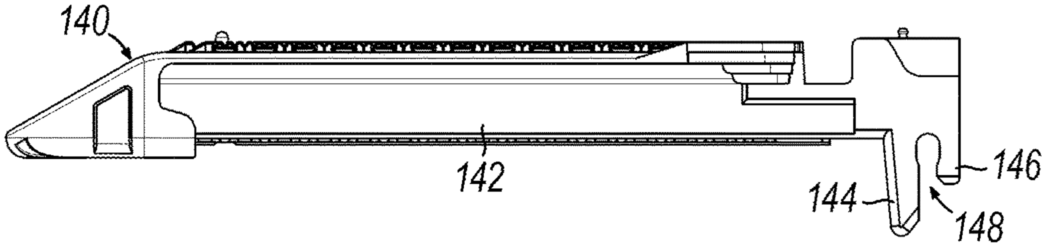
FIG. 16 depicts a side elevational view of the staple cartridge of FIG. 9.

As shown in FIG. 15, each pair of staple drivers (172) of staple cartridge (140) is integrally formed as a staple driver unit (170) having a bridge feature (174) that interconnects staple drivers (172) at their lower ends. Staple drivers (172) of driver unit (170) are arranged in a staggered formation in which staple drivers (172) are laterally and longitudinally offset from one another, relative to the longitudinal axis of staple cartridge (140), such that staple drivers (172) are configured to align with respective staple openings (166) of cartridge body (142). Each staple driver (172) includes a groove (176) at its upper end configured to receive and support the crown of a respective staple (168). Additionally, each staple driver (172) includes at its upper end staple leg receiving features in the form of pockets (178) that are defined by respective chamfered surfaces and are configured to receive staple leg tips of a respective staple (168) during formation of staple (168) by anvil plate (72) when stapler (10) is fired. Such features are described in greater detail in U.S. Pat. No. 11,229,433, incorporated by reference above.

As described above, coupling legs (144, 146) formed at the proximal end of staple cartridge (140) facilitate coupling of staple cartridge (140) with distal jaw portion (20) of cartridge channel (16). More specifically, each lateral side of staple cartridge (140) includes a longer distal coupling leg (144) and a shorter proximal coupling leg (146), separated by a gap (148). Gap (148) is suitably positioned and shaped, for example with an oval-like shape, to provide proximal coupling leg (146) with a smaller minimum thickness in a longitudinal direction than distal coupling leg (144), thus rendering proximal coupling leg (146) suitably flexible relative to cartridge body (142). Accordingly, during installation of staple cartridge (140) into distal jaw portion (20), proximal coupling leg (146) is configured to deflect relative to distal coupling leg (144) to enable clamp lever pivot pin (42) to be received into gap (148) with a snap-fit engagement and with a suitable degree of installation force by the user.

Figure 17:
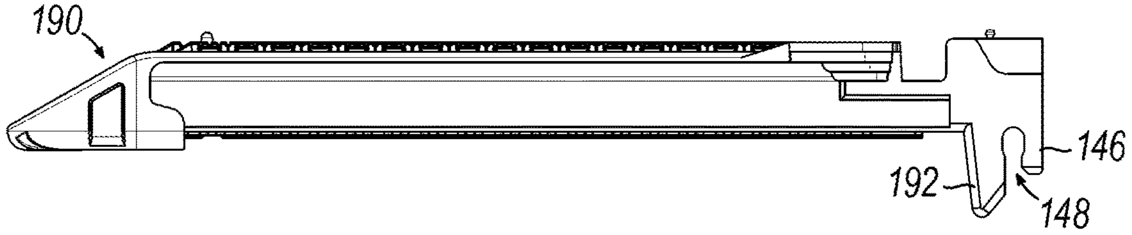
FIG. 17 depicts a side elevational view of another illustrative staple cartridge configured for use with a linear surgical stapler.
Figure 18:
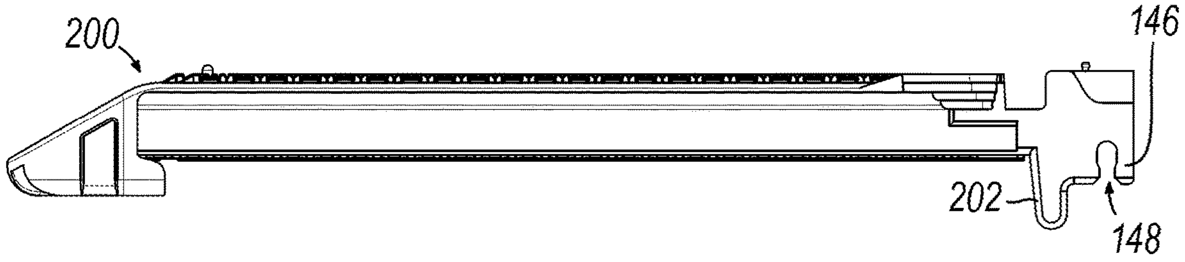
FIG. 18 depicts a side elevational view of another illustrative staple cartridge configured for use with a linear surgical stapler.

Distal coupling leg (144) of staple cartridge (140) may also serve as a poka-yoke feature that is sized and shaped to render staple cartridge (140) usable with only a predetermined type of linear surgical stapler, such as a stapler configured to apply to tissue a staple pattern and cut line of a predetermined length (e.g., 60 mm). FIG. 17 shows another illustrative staple cartridge (190) that is generally similar to staple cartridge (140), except that staple cartridge (190) is longer and has a uniquely shaped distal coupling leg (192) that renders staple cartridge (190) usable with only another predetermined type of linear surgical stapler, such as a stapler configured to apply a longer (e.g., 80 mm) staple pattern and cut line to tissue. FIG. 18 shows yet another illustrative staple cartridge (200) that is generally similar to staple cartridges (140, 190), except that staple cartridge (200) is even longer and has a uniquely shaped distal coupling leg (202) that renders staple cartridge (200) usable with only another predetermined type of linear surgical stapler, such as a stapler configured to apply an even longer (e.g., 100 mm) staple pattern and cut line to tissue.

Staple cartridges (140, 190, 200) may be further configured in accordance with the teachings of U.S. patent application Ser. No. 29/842,580, entitled "Staple Cartridge for Linear Surgical Stapler," filed Jun. 14, 2022 and issued as U.S. Pat. No. D1,067,431 on Mar. 18, 2025, the disclosure of which is incorporated by reference herein.

C. Illustrative Use of Linear Surgical Stapler

Figure 5:
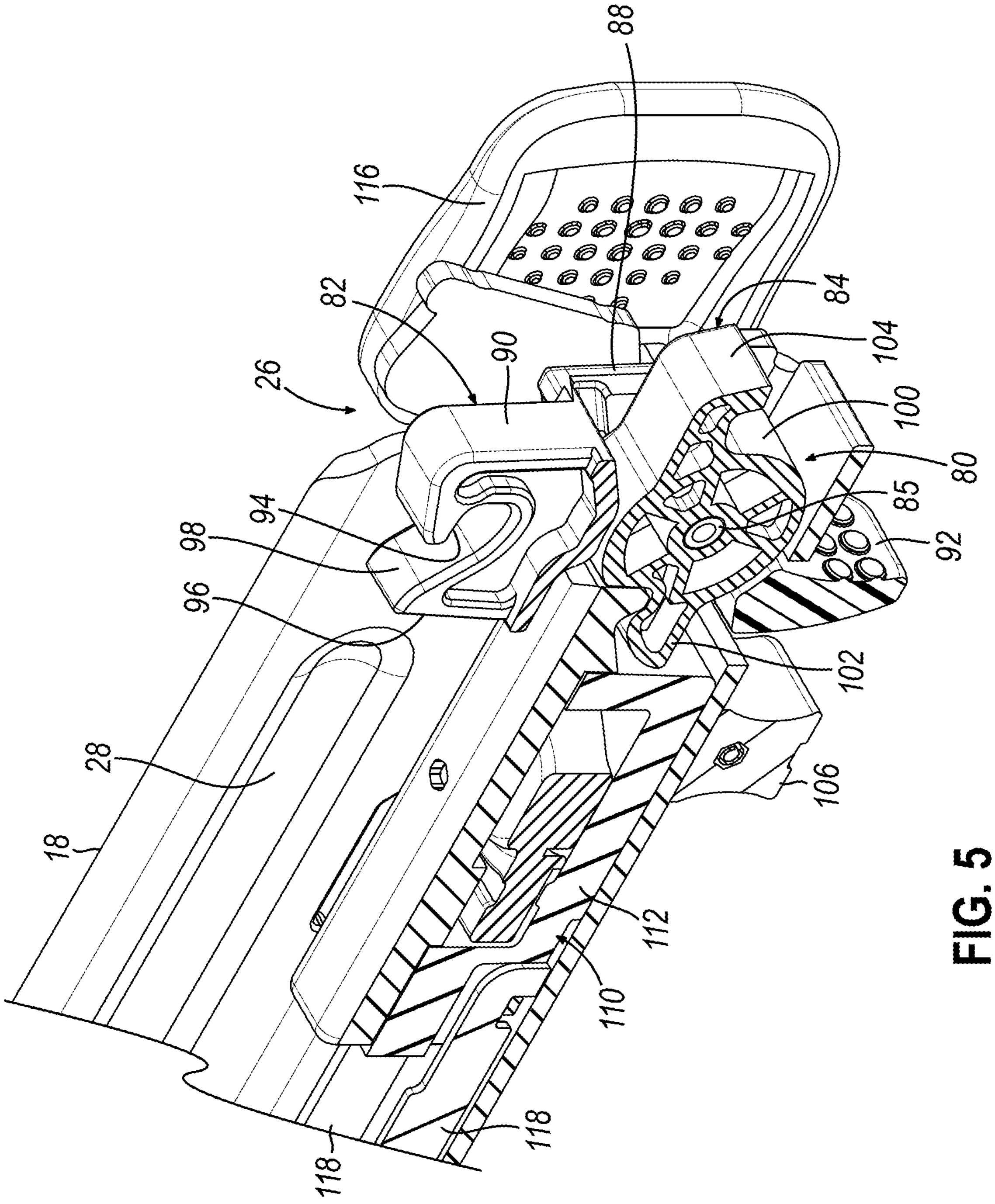
FIG. 5 depicts a cross-sectional perspective view of a proximal portion of the cartridge half of the linear surgical stapler of FIG. 1 with the clamp lever in an open position to reveal details of a firing assembly and a retaining assembly of the cartridge half.
Figure 6:
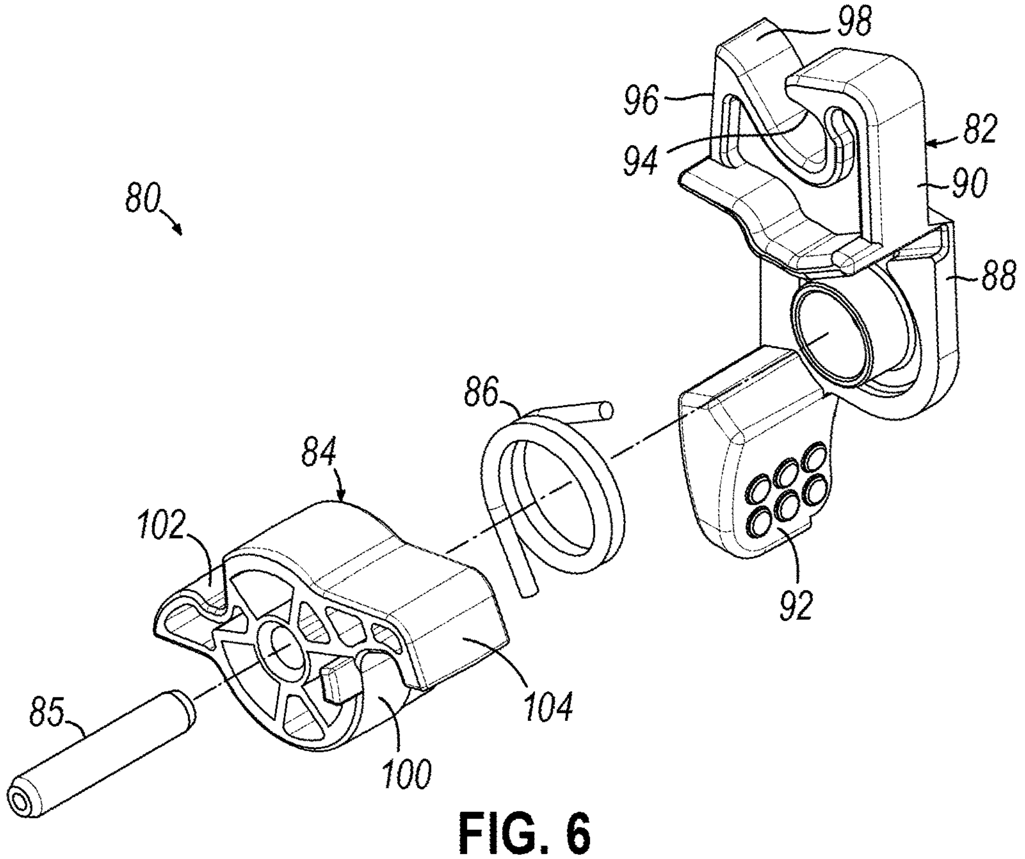
FIG. 6 depicts an exploded perspective view of the retaining assembly of FIG. 5.
Figure 7:
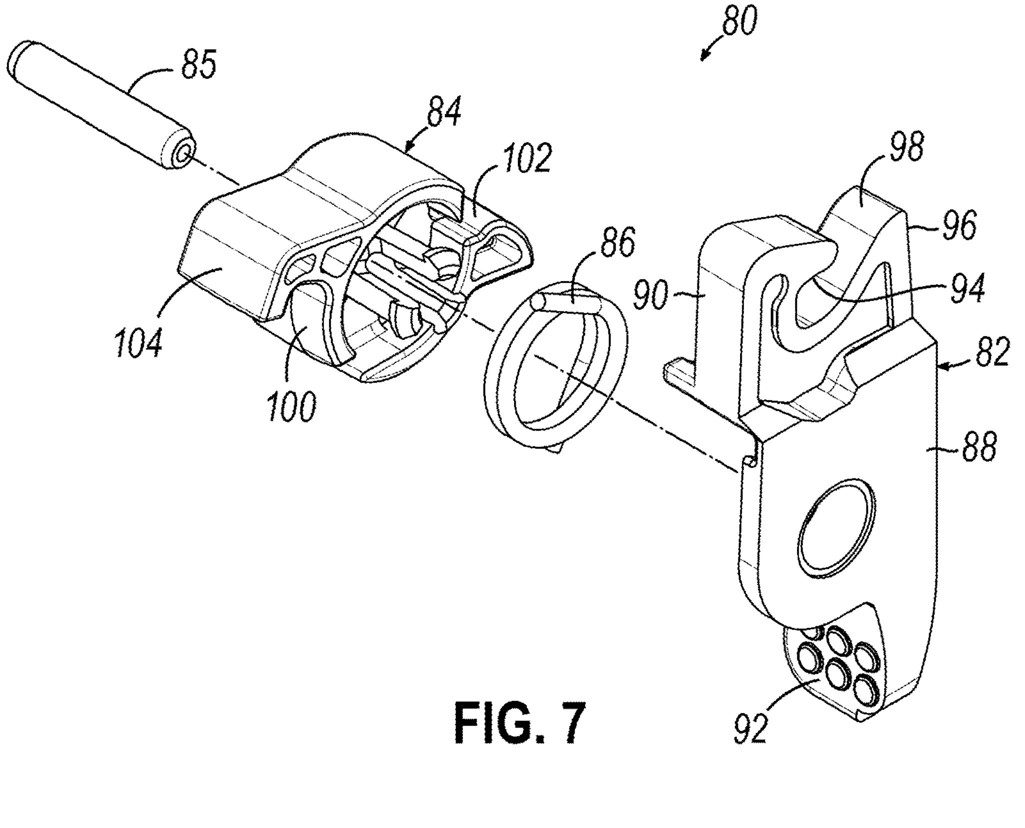
FIG. 7 depicts another exploded perspective view of the retaining assembly of FIG. 5.

FIGS. 19A-19E show illustrative coupling of stapler halves (12, 14) and subsequent firing of assembled stapler (10) during a surgical procedure. As shown in FIG. 9A, clamp lever (40) of cartridge half (12) is provided in the open position so that jaw slots (50) align with vertical slots (24) of cartridge channel side flanges (22). Additionally, firing assembly (110) is maintained in its proximal home position by detent member (84) of retaining assembly (80), as shown in FIG. 5 described above. At this stage, a section of tissue (not shown) to be stapled and cut may be positioned over the top of staple cartridge (140) disposed in distal jaw portion (20) of cartridge half (12). Alternatively, the tissue may be positioned over staple cartridge (140) following coupling of the proximal ends of stapler halves (12, 14), described below.

As shown in FIGS. 19A-19B, the proximal ends of stapler halves (12, 14) are aligned with one another, and proximal anvil pin (70) is directed downwardly into proximal tapered notches (26) of cartridge channel (16) to engage latch finger (90) of anvil latch member (82). This engagement forces anvil latch member (82) to resiliently rotate clockwise, thus enabling latch finger (90) to capture anvil pin (70) and thereby releasably couple together the proximal ends of stapler halves (12, 14), as seen in FIG. 19B. With clamp lever (40) still in the open position as shown in FIG. 19B, stapler (10) is provided in a "hang-open" state such that stapler (10) may be held single-handedly by anvil half (14) while cartridge half (12) remains coupled to anvil half (14). As shown in FIG. 9C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

Figure 19D:
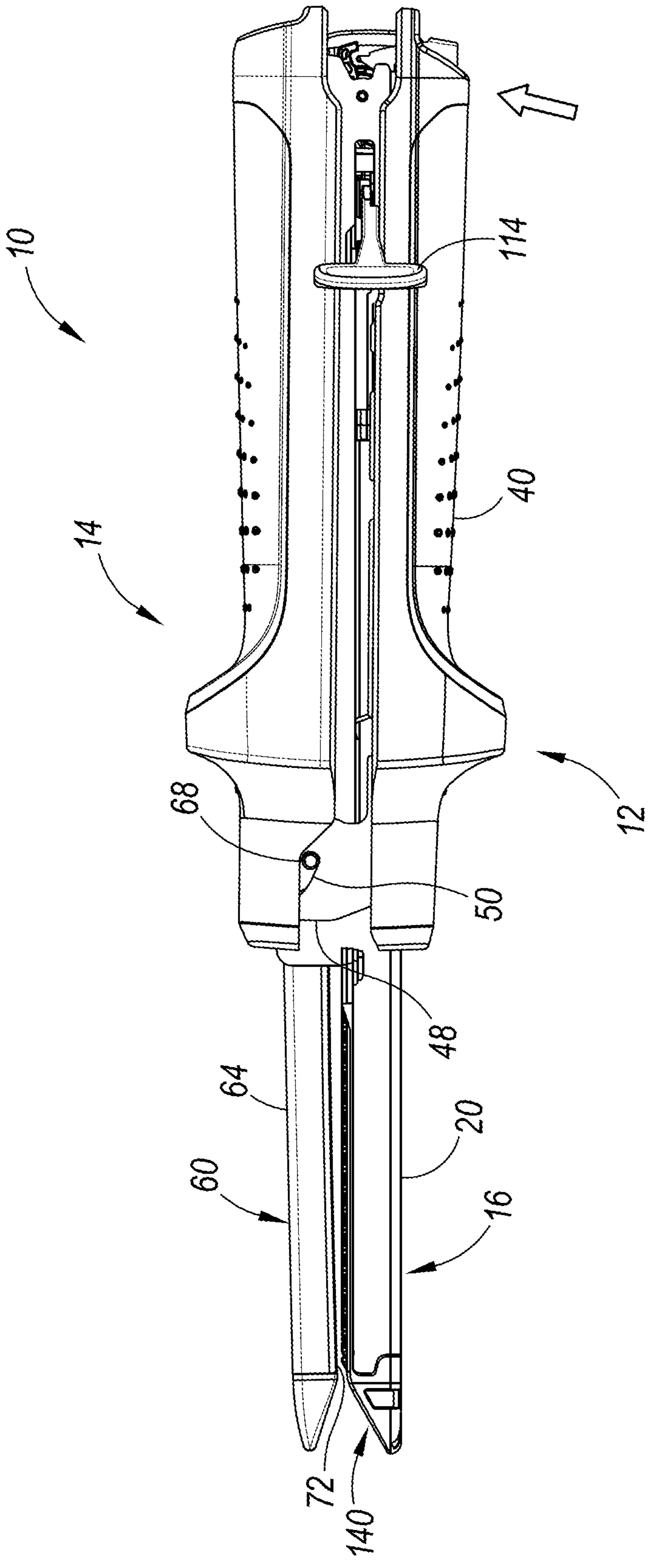
FIG. 19D depicts a side elevational view of the linear surgical stapler of FIG. 1, showing closure of the clamp lever to fully clamp the stapler halves together.

As shown in FIG. 19D, clamp lever (40) is closed to draw anvil latch pin (68) against the closed proximal ends of jaw slots (50) and thereby fully clamp anvil half (14) against cartridge half (12), with tissue (not shown) clamped between the stapling surfaces defined by staple cartridge (140) and anvil plate (72). A slight transverse gap is defined between staple cartridge (140) and anvil plate (72) by a tissue gap post (162) of staple cartridge (140), thus accommodating the tissue therebetween with a predetermined degree of tissue compression. As shown in FIGS. 19A and 19B, tissue gap post (162) is disposed at a distal end of staple cartridge (140) and is configured to contact a distal end of anvil plate (72) when stapler (10) is in the fully clamped state shown in FIG. 19D. In response to clamp lever (40) reaching the fully closed position, clamp lever latch member (54) may rotate to capture a proximal end of a base wall of cartridge channel (16) and thereby assume a latched state in which clamp lever latch member (54) maintains clamp lever (40) in the closed position.

Figure 19E:
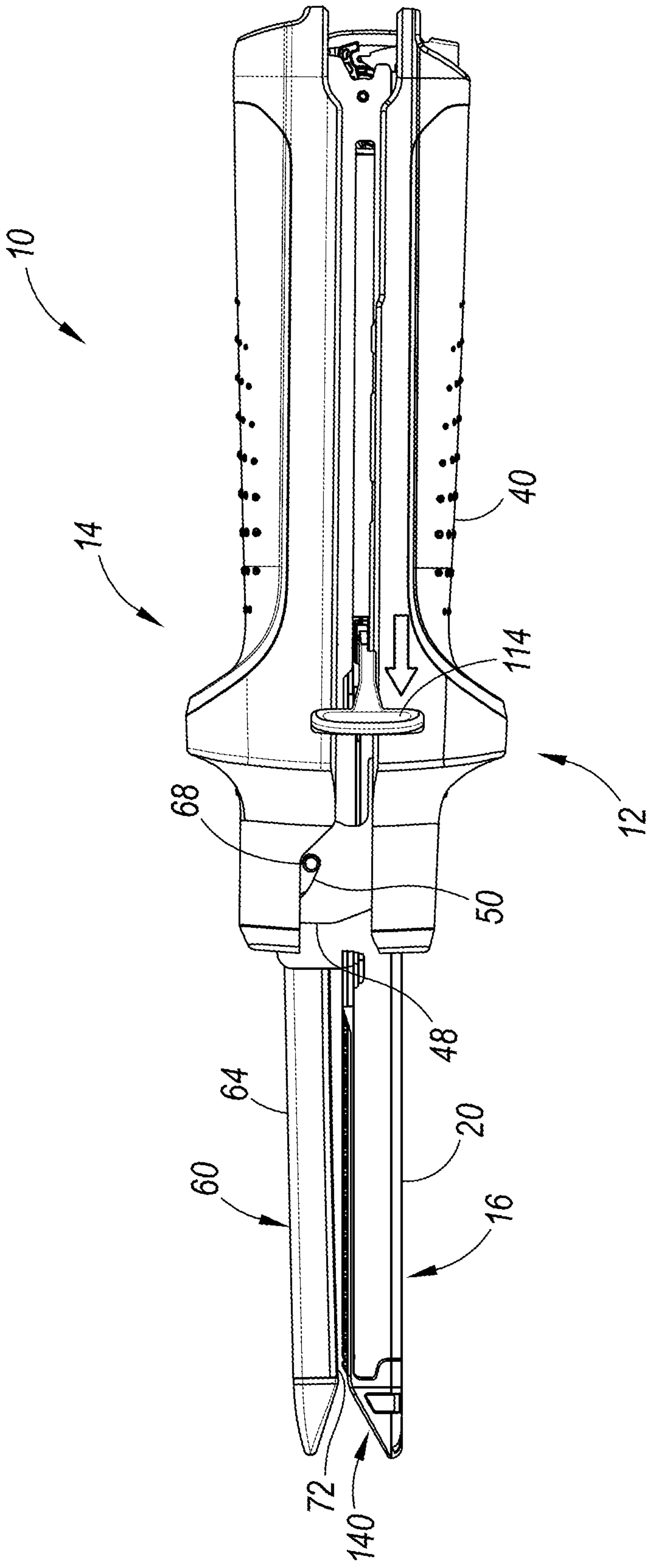
FIG. 19E depicts a side elevational view of the linear surgical stapler of FIG. 1, showing distal actuation of the firing assembly while the stapler halves are in the fully clamped state.

As shown in FIG. 19E, upon reaching the fully clamped state, stapler (10) may be fired by driving a deployed actuator (114, 116) of firing assembly (110) distally along proximal frame portion (18) of cartridge half (12). This action causes elongate beams (118, 122) of firing assembly (110) to translate distally through corresponding channels formed in staple cartridge (140) and thereby fire staples into the clamped tissue via cam ramps (120) and staple drivers (172), and simultaneously cut the clamped tissue with knife member (126). Following completion of the firing stroke, firing assembly (110) is returned to its proximal home position via the actuator (114, 116). Clamp lever latch member (54) may then be depressed to release the proximal end of clamp lever (40) from cartridge channel (16), thus permitting clamp lever (40) to be re-opened. Then, release button (92) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include additional features to promote decoupling of stapler halves (12, 14), for example as disclosed in U.S. Pat. No. 11,033,266, incorporated by reference above.

D. Linear Surgical Stapler Having Hang-Open Feature and Clamp Lever Latch Inhibiting Feature As described above in connection with linear surgical stapler (10), a pivotable coupling is established between the proximal ends of stapler halves (12, 14) when anvil pin (70) is captured by anvil latch member (82). Additionally, clamp lever latch member (54) is configured to releasably capture a proximal end of a base wall of cartridge channel (16) to retain clamp lever (40) in its closed position during firing.

In some instances, it may be desirable to provide a linear surgical stapler with the ability to assume an open state in which the respective elongate members of the stapler halves assume a predetermined maximum angular orientation relative to one another and remain releasably coupled together at their proximal ends (referred to as a "hang-open" or "open aperture" state), such that the stapler in the assembled yet open state can be easily manipulated by an operator with a single hand. It may also be desirable to inhibit latching of the clamp lever latch member when the firing assembly is displaced from its proximal home position, to serve as an indicator to a user that the staple cartridge may have already been at least partially fired and thus not suitable for use in a surgical procedure. The following description provides an illustrative example of a variation of linear surgical stapler (210) that provides such functionality.

Figure 21:
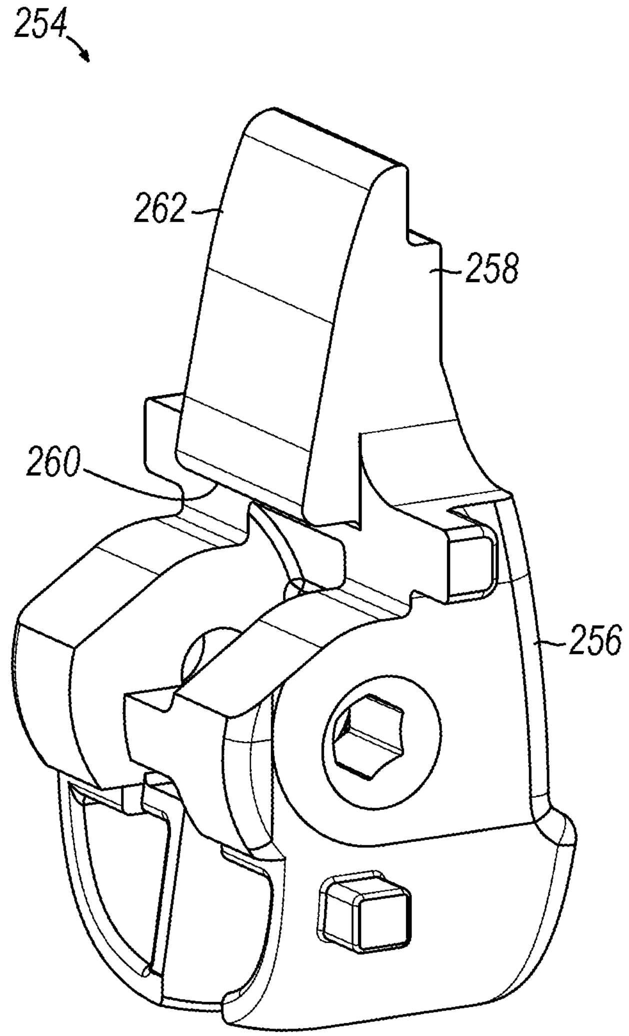
FIG. 21 depicts a perspective view of a clamp lever latch member of the linear surgical stapler of FIG. 20.

FIG. 20 shows a proximal portion of another illustrative linear surgical stapler (210) that includes a cartridge half (212) and an anvil half (214), which are similar to cartridge half (12) and anvil half (14) of linear surgical stapler (10) described above except as otherwise described below. In particular, cartridge half (212) includes a clamp lever (240) having a clamp lever latch member (254) that is configured to inhibit latching of the proximal end of clamp lever (240) to the proximal end of cartridge channel (216) when clamp lever (240) is closed unless firing assembly (310) is in its proximal home position. As shown in FIG. 21, clamp lever latch member (254) includes a latch member body (256) that pivotably couples with clamp lever (240), and a tapered projection (258) that extends upwardly from latch member body (256). Tapered projection (258) includes a lower edge (260) configured to hook onto the proximal end of a base wall of cartridge channel (216) of cartridge half (212) and thereby retain clamp lever (240) in a closed state. Tapered projection (258) further includes a convexly curved cam surface (262) that faces distally.

Figure 22:
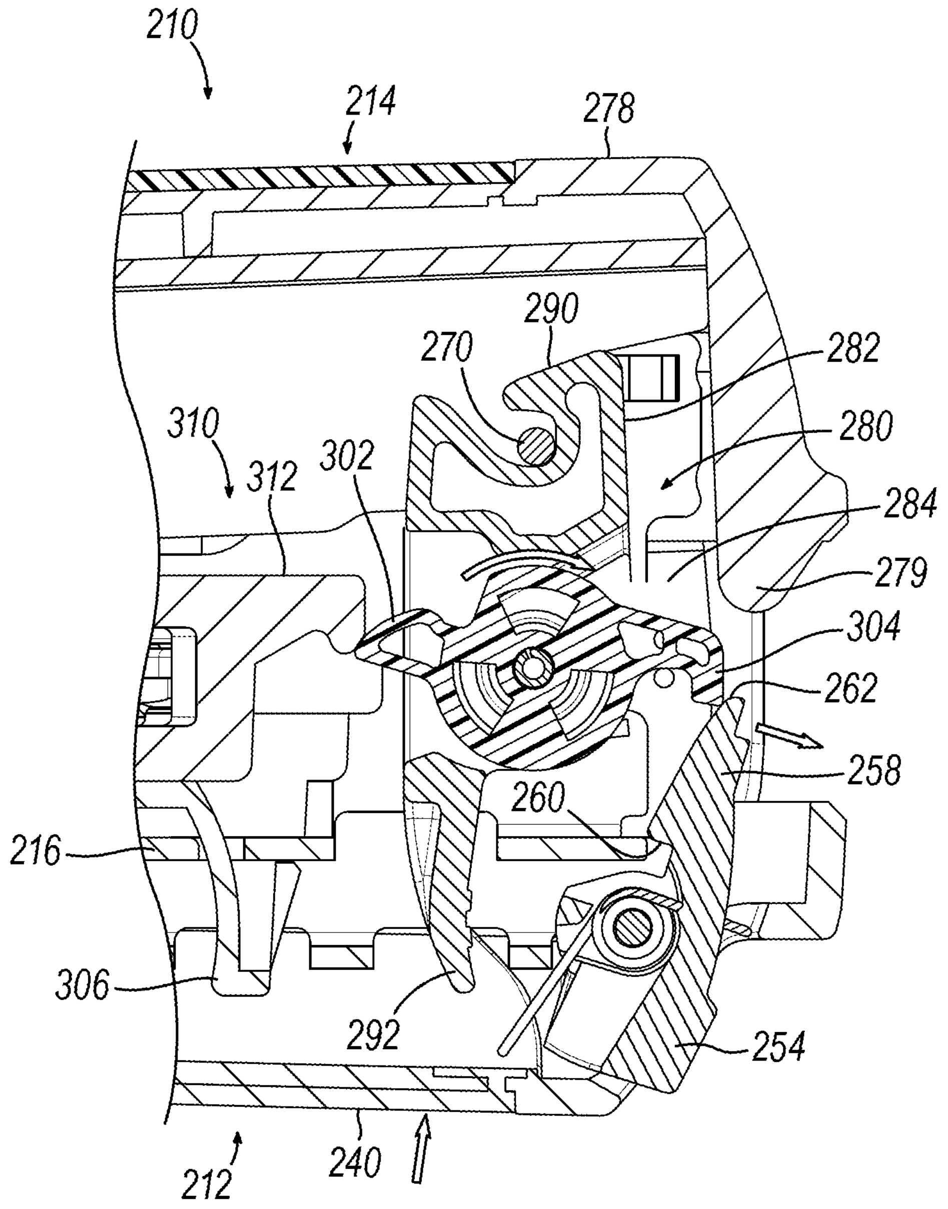
FIG. 22 depicts a side cross-sectional view of the proximal portion of the linear surgical stapler of FIG. 20, showing details of a firing assembly, a retaining assembly, and the clamp lever latch member of the cartridge half, showing the clamp lever in the fully closed position with the latch member in an unlatched state while the firing assembly is displaced from a proximal home position.
Figure 23:
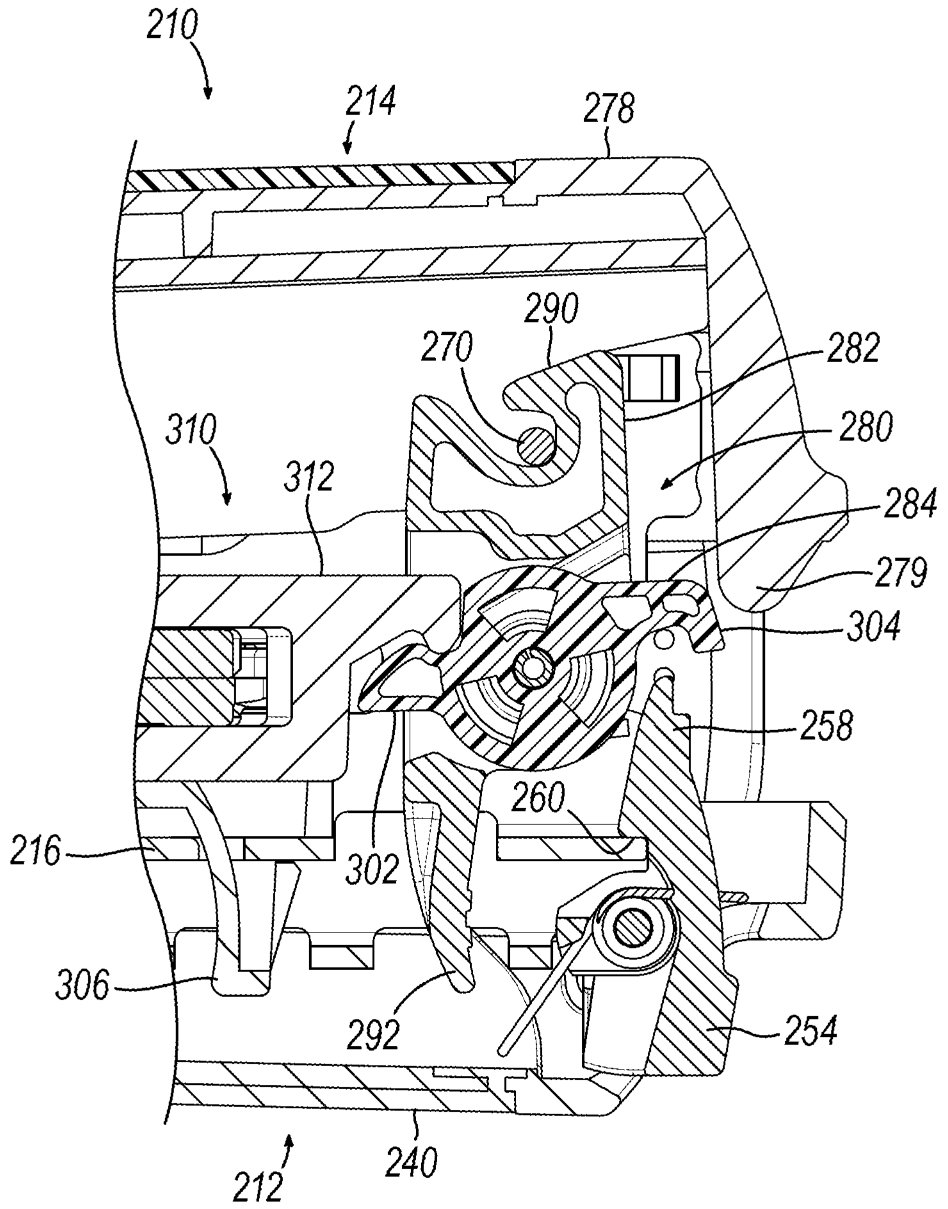
FIG. 23 depicts a side cross-sectional view of the proximal portion of the linear surgical stapler of FIG. 20, showing the latch member in the latched state while the firing assembly is in the proximal home position.

As shown in FIG. 22, when firing assembly (310) is displaced distally from its proximal home position, the proximal end of the firing assembly slide block (312) is disengaged from distal finger (302) of detent member (284). Via the resilient bias of torsion spring (286), detent member (284) rotates clockwise to a rotational position in which its proximal hook (304) is lowered. When clamp lever (240) is then moved from the open position to the closed position while firing assembly (310) is in this distally displaced state, the proximal end of proximal hook (304) contacts cam surface (262) of clamp lever latch member (254). This camming interaction drives tapered projection (258) of clamp lever latch member (254) away from cartridge channel (216) and thus prevents clamp lever latch member (254) from latching onto the proximal end of cartridge channel (216). This result may alert the user that firing assembly (310) is displaced from its proximal home position such that staple cartridge (140) may already be partially fired and thus not suitable for use on a patient. In response, the user may then return the firing assembly (310) to its proximal home position, substitute in a fresh staple cartridge (140), and proceed with the surgical procedure. With firing assembly (310) in its proximal home position as shown in FIG. 23, detent member (284) is maintained by slide block (312) in a counter-clockwise rotational position in which proximal hook (104) is raised. Accordingly, clamp lever latch member (254) may avoid contact with proximal hook (304) and latch onto the proximal end of cartridge channel (216) when clamp lever (240) is closed.

Figure 24:
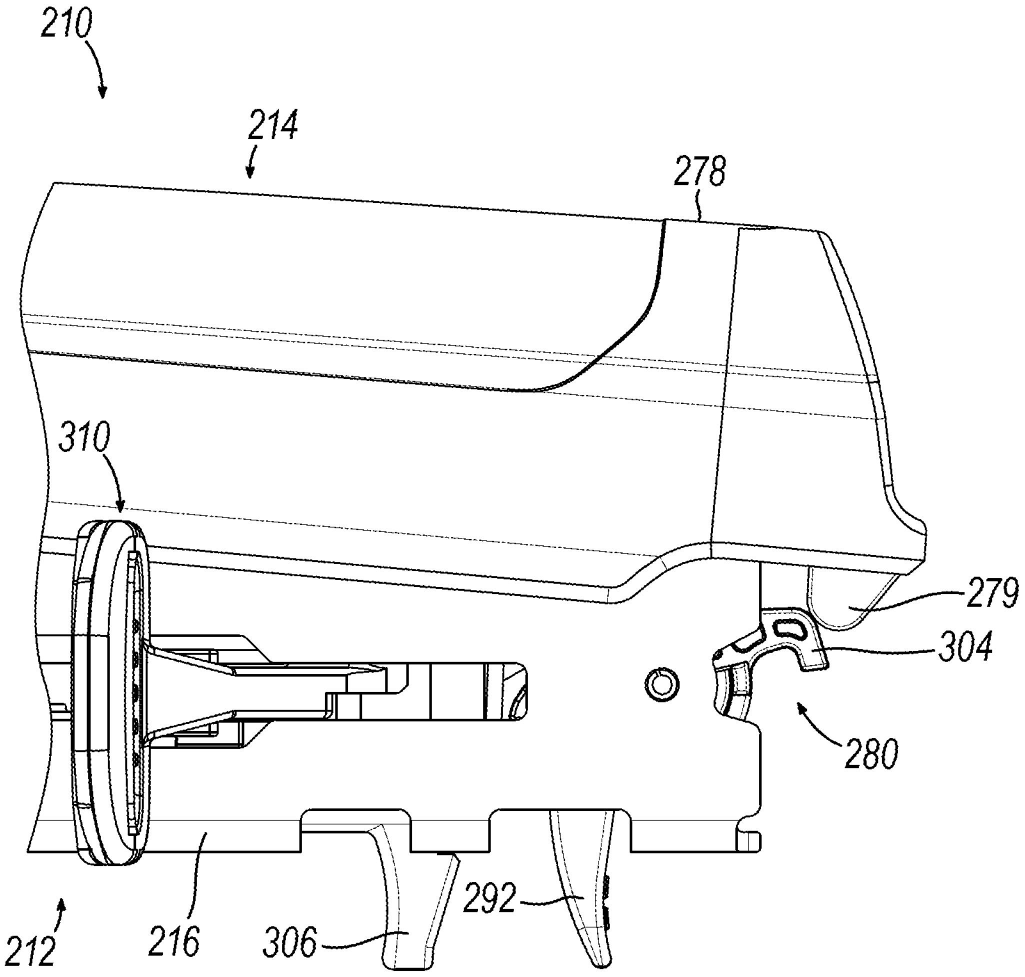
FIG. 24 depicts a side elevational view of the proximal portion of the linear surgical stapler of FIG. 20, showing a protrusion located at a proximal end of a shroud of the anvil half and contacting a retaining member of the cartridge half to resist decoupling of the proximal ends of the stapler halves when the stapler is in the hang-open state.

As shown in FIG. 24, anvil half (214) of stapler (210) further includes an anvil shroud (278) having a protrusion in the form of a rib (279) that extends downwardly from a proximal end of anvil shroud (278). Rib (279) includes a rounded tip that is configured to contact a proximal surface of proximal hook (304) of retaining assembly (280) of cartridge half (212) when stapler (210) is held by anvil half (214) in a hang-open state similar to the hang-open state shown in FIG. 19B. The engagement between rib (279) and proximal hook (304) of dent member (284) in the hang-open state provides a resistance to decoupling of the stapler halves (212, 214). More specifically, in the hang-open state, proximal anvil pin (270) exerts an upward prying force against the underside latching surface (294) of latch finger (290) of anvil latch member (282), which causes anvil latch member (282) to rotate clockwise release anvil pin (270) and decouple stapler halves (212, 214). The interaction between rib (279) and proximal hook (304) of detent member (284) effectively counteracts and lessens this upward prying force, thereby providing resistance to decoupling of stapler halves (212, 214) and enabling stapler (210) to remain in the hang-open state more securely without unintentional decoupling. Such a configuration may be particularly beneficial for versions of stapler (210) in which cartridge half (212) has an increased weight, due to size and/or material selection, that results in an increase prying force being exerted between proximal anvil pin (270) and anvil latch member (282) in the hang-open state.

E. Linear Surgical Stapler Having Clamp Lever with Missed-Latch Indication Features As described above in connection with linear surgical stapler (10), when latch pin (68) is properly aligned with jaw slots (50), actuation of clamp lever (40) from the open position to the closed position (see FIG. 19C-19D) operates to cammingly drive the opposed lateral ends of latch pin (68) proximally within jaw slots (50) and thereby clamp stapler halves (12, 14) together to approximate stapling surfaces (72, 140). In some instances, it may be difficult for the surgeon to sufficiently approximate stapler halves (12, 14) to properly align latch pin (68) with jaw slots (50), such as when clamping on thick tissue, and the surgeon may unknowingly close clamp lever (40) without properly capturing latch pin (68), such that stapler halves (12, 14) are not properly latched together. Accordingly, it may be desirable to provide stapler (10) with one or more features that are configured provide to the surgeon a clear indication when latch pin (68) has not been properly captured within jaw slots (50), and that readjustment of clamp lever (40) is required to achieve proper clamping on tissue.

Figure 25A:
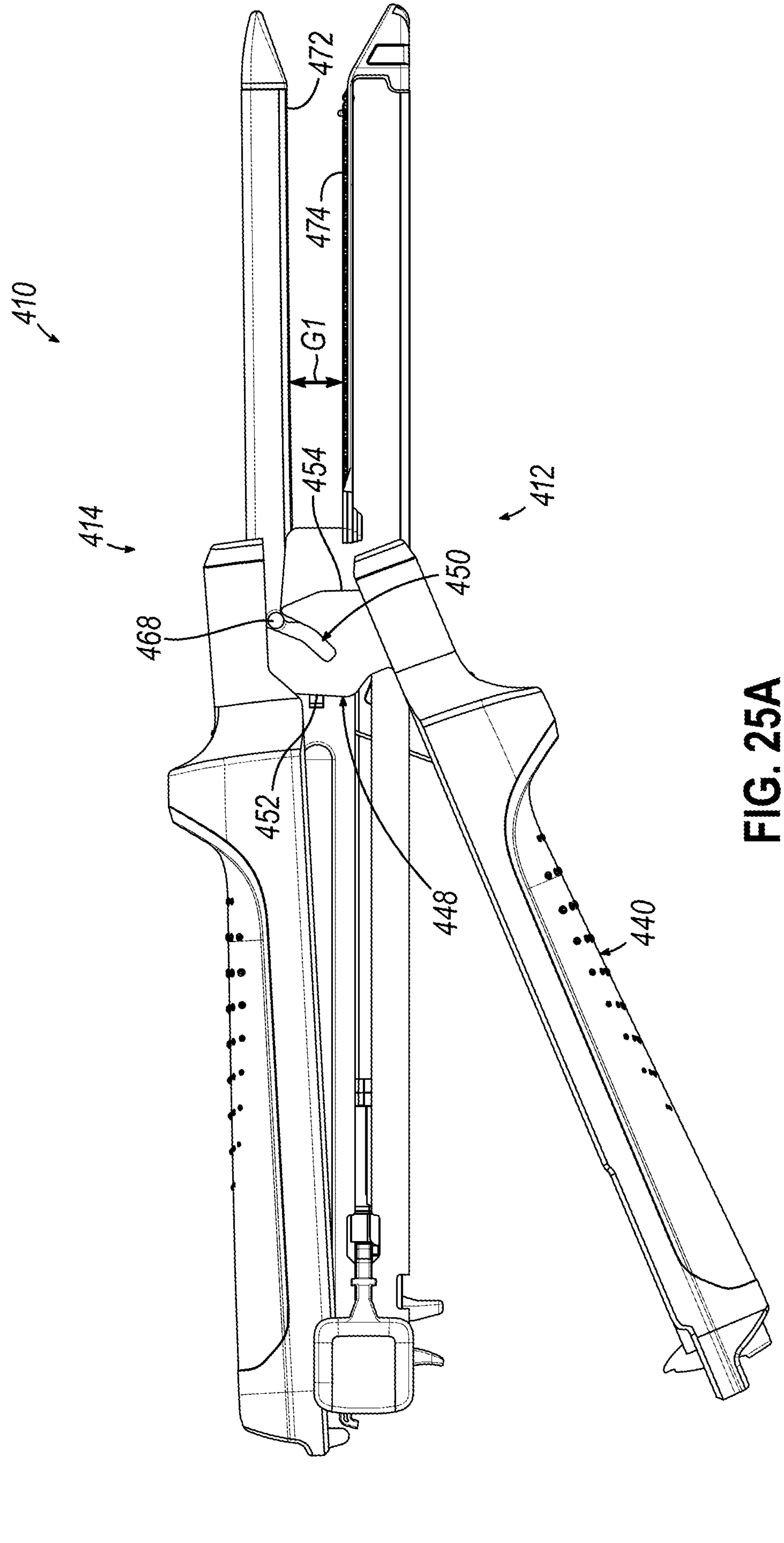
FIG. 25A depicts a side elevational view of a second illustrative linear surgical stapler, showing a clamp lever of the stapler in an open position.
Figure 25B:
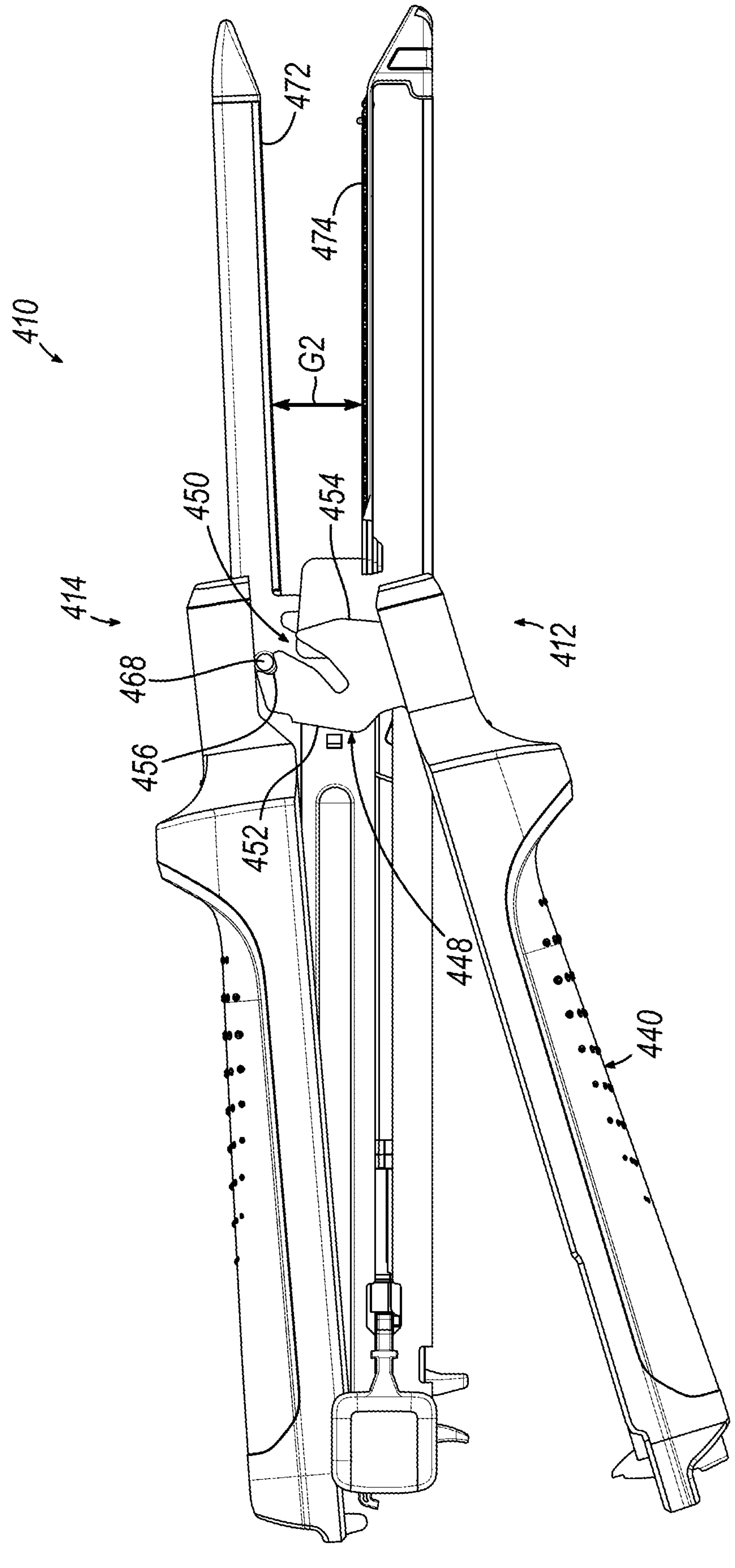
FIG. 25B depicts a side elevational view of the linear surgical stapler of FIG. 25A, showing the clamp lever in a partially closed, non-latched position.
Figure 25C:
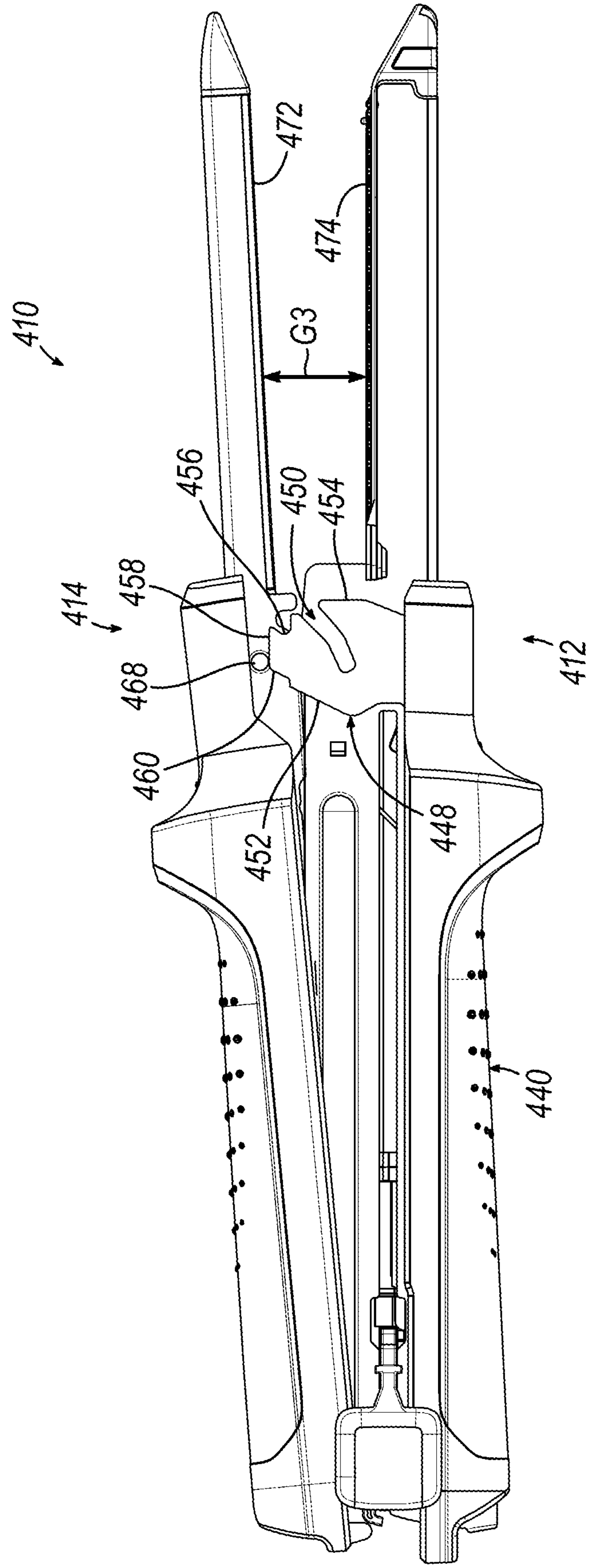
FIG. 25C depicts a side elevational view of the linear surgical stapler of FIG. 25A, showing the clamp lever in a fully closed, non-latched position.

FIGS. 25A-25C show another illustrative linear surgical stapler (410) that includes a cartridge half (412) and an anvil half (414) that are similar to cartridge half (12) and anvil half (14) of linear surgical stapler (10) described above except as otherwise described below. In particular, clamp lever (440) of cartridge half (412) includes a laterally opposed pair of jaws (448) that are uniquely shaped to provide to a surgeon a clear indication when latch pin (68) has not been properly aligned with and captured by jaw slots (450) during closure of clamp lever (440).

Referring briefly to FIG. 25C, each jaw (448) includes a first pin engagement feature (also referred to as a first engagement portion) in the form of a curved slot (450) having a closed proximal end and an open distal end configured to receive a respective lateral end of latch pin (68). Each jaw slot (450) divides its respective jaw (448) into an upper jaw portion (452) and a lower jaw portion (454) that are interconnected along a proximal side of jaw (448). Each upper jaw portion (452) at its distal end includes a second pin engagement feature in the form of a recess (456) that is generally semi-circular in shape and is sized to releasably capture a respective lateral end of latch pin (68) when latch pin (68) is mis-aligned with jaw slots (450), as described further below. Additionally, upper jaw portion (452) has an angled outer profile such that a width of upper jaw portion (452) measured transversely between jaw slot (450) and an outer surface (458) increases proximally from a distal end of jaw (448) toward an apex (460) of upper jaw portion (452) that is approximately aligned with a mid-length point of slot (450), before then decreasing. Accordingly, a maximum such width of upper jaw portion (452) is defined at apex (460). As described in greater detail below, each of recess (456) and outer surface (458) is configured to engage latch pin (68) when latch pin (68) is misaligned with jaw slots (450) so as to indicate to the surgeon that latch pin (68) has not been properly captured by jaw slots (450) and that readjustment of stapler halves (412, 414) is required.

FIG. 25A shows an illustrative scenario in which stapler halves (412, 414) have been sufficiently approximated such that latch pin (68) is properly aligned with and capturable by jaw slots (450). Stapling surfaces (472, 474) are situated in a partially approximated state that defines a gap (G1) at a mid-length point of the staple cartridge. In this scenario, clamp lever (440) may then be closed to properly clamp stapler halves (412, 414) together and fully approximate stapling surfaces (472, 474), such as shown in FIGS. 19C-19D in connection with linear surgical stapler (10).

FIG. 25B shows an alternative scenario in which a surgeon has failed sufficiently approximate stapler halves (412, 414) during clamping such that latch pin (68) is just slightly misaligned with and not capturable by jaw slots (450). When the surgeon then attempts to close clamp lever (440), latch pin (68) is captured by jaw recesses (456) such that clamp lever (440) is inhibited from closing and is constrained in an intermediate position between its open position and its closed position. This situates stapling surfaces (472, 474) in a spaced-apart state in which they define a second gap (G2) at the mid-length point of the staple cartridge, where the second gap (G2) is noticeably larger than the first gap (G1) of FIG. 25A. This provides the surgeon with a visible and tactile indication that clamp lever (440) is not properly aligned with latch pin (68) and must be reopened and adjusted to achieve proper clamping together of stapler halves (412, 414).

FIG. 25C shows yet another alternative scenario in which a surgeon has failed to sufficiently approximate stapler halves (412, 414) during clamping such that latch pin (68) is more substantially misaligned with and not capturable by jaw slots (450). In this scenario, clamp lever (440) has been permitted to pivot to its closed position while latch pin (68) has simultaneously tracked proximally along the outer surface (458) of each upper jaw portion (452), via rotation of jaw (448) relative to latch pin (468), and ultimately rest at apex (460) when clamp lever (440) is fully closed. The angled outer profile of upper jaw portions (452) acts as a camming feature that urges the distal end of anvil half (412) away from the distal end of cartridge half (412) as clamp lever (440) is closed latch pin (68) approaches apex (460) along outer surface (458). This situates stapling surfaces (472, 474) in an even further spaced-apart state in which they define a third gap (G3) at the mid-length point of the staple cartridge, where the third gap (G3) is noticeably larger than the second gap (G2) of FIG. 25B. Thus, the surgeon is provided with a visible indication that stapler (410) is not properly latched and that clamp lever (440) must be reopened to properly approximate stapler halves (412, 414) so that latch pin (68) may be properly aligned with and received by jaw slots (450) before clamp lever (440) is reclosed.

F. Alternative Missed-Latch Indication Features

Figure 26A:
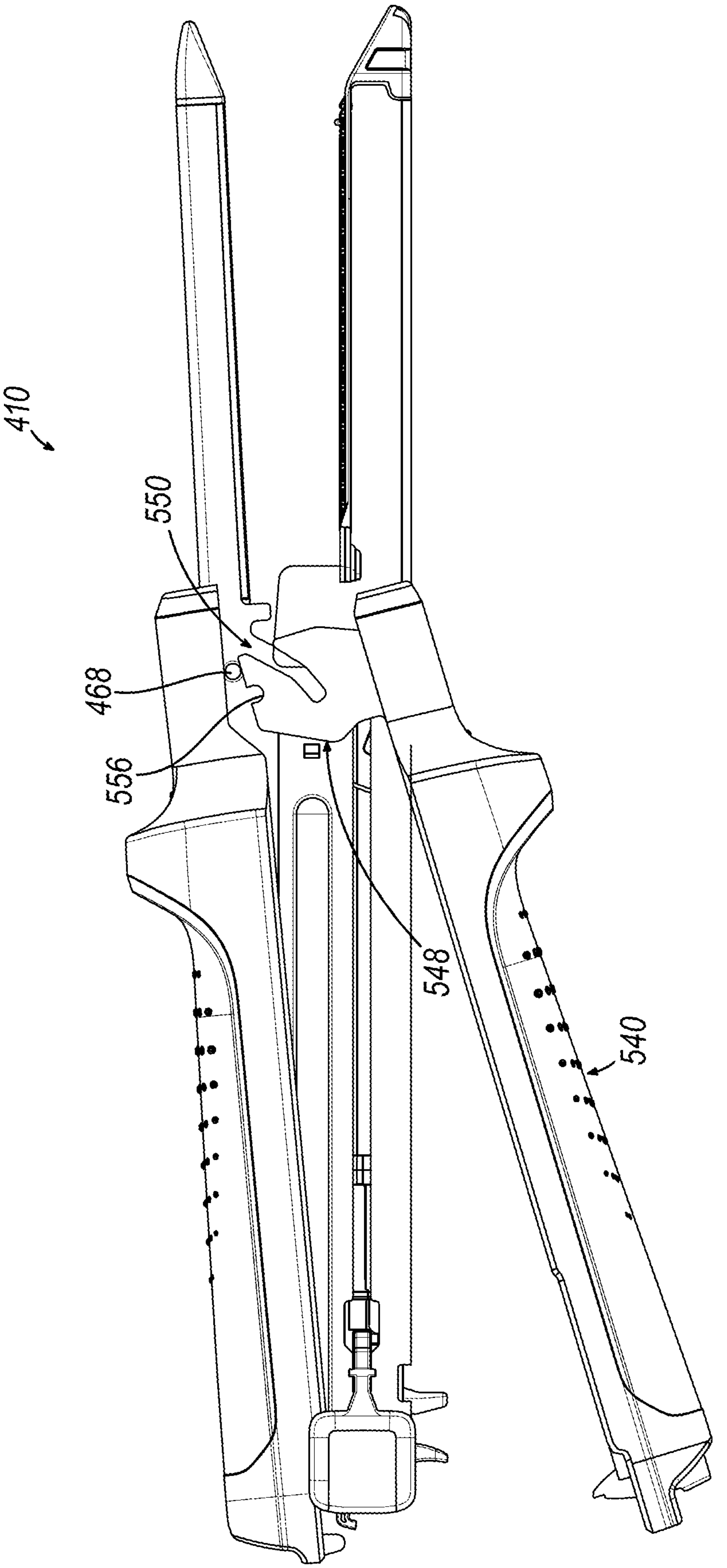
FIG. 26A depicts a side elevational view of a third illustrative linear surgical stapler, showing a clamp lever in a partially closed, non-latched position.
Figure 26B:
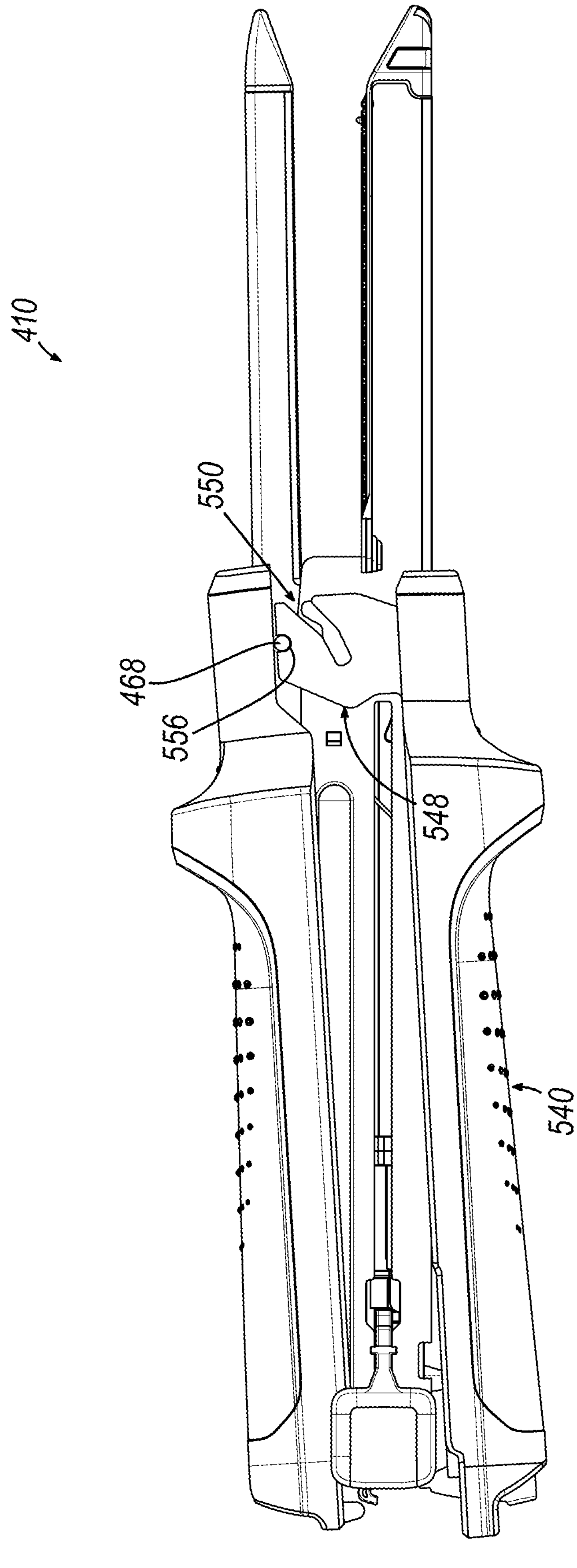
FIG. 26B depicts a side elevational view of the linear surgical stapler of FIG. 26A, showing the clamp lever in another partially closed, non-latched position.

FIGS. 26A-26B show an illustrative linear surgical stapler (410) that includes a different clamp lever (540). Clamp lever (540) is substantially similar to clamp lever (440) but with the following differences. Similar to clamp lever (440), clamp lever (540) includes a laterally opposed pair of jaws (548) that are uniquely shaped to provide to a surgeon a clear indication when latch pin (468) has not been properly aligned with and captured by jaw slots (550) during closure of clamp lever (540).

FIG. 26A depicts latch pin (468) positioned between jaw slot (550) and a second latch pin engagement feature in the form of a recess (556) formed in an upper side of an upper portion of respective jaw (548). In this orientation, clamp lever (540) is unable to transition into a fully closed configuration and thus remains only partially closed. Recess (556) may include a semi-circular profile and be spaced a distance from jaw slot (550). Recess (556) may be of the same or similar thickness to jaw slot (550). As shown in FIG. 26B, recess (556) is configured to capture latch pin (468) during a misalignment of latch pin (468) with jaw slots (550) to thus prevent clamping and subsequent firing of stapler (410). As shown, once latch pin (468) has been captured within recess (556), clamp lever (540) remains in a partially closed configuration. By reopening clamp lever (540), latch pin (468) may then be released from recess (556) and be properly aligned in jaw slot (550) to thus transition stapler (410) from the unclamped state to the fully clamped state.

Figure 27:
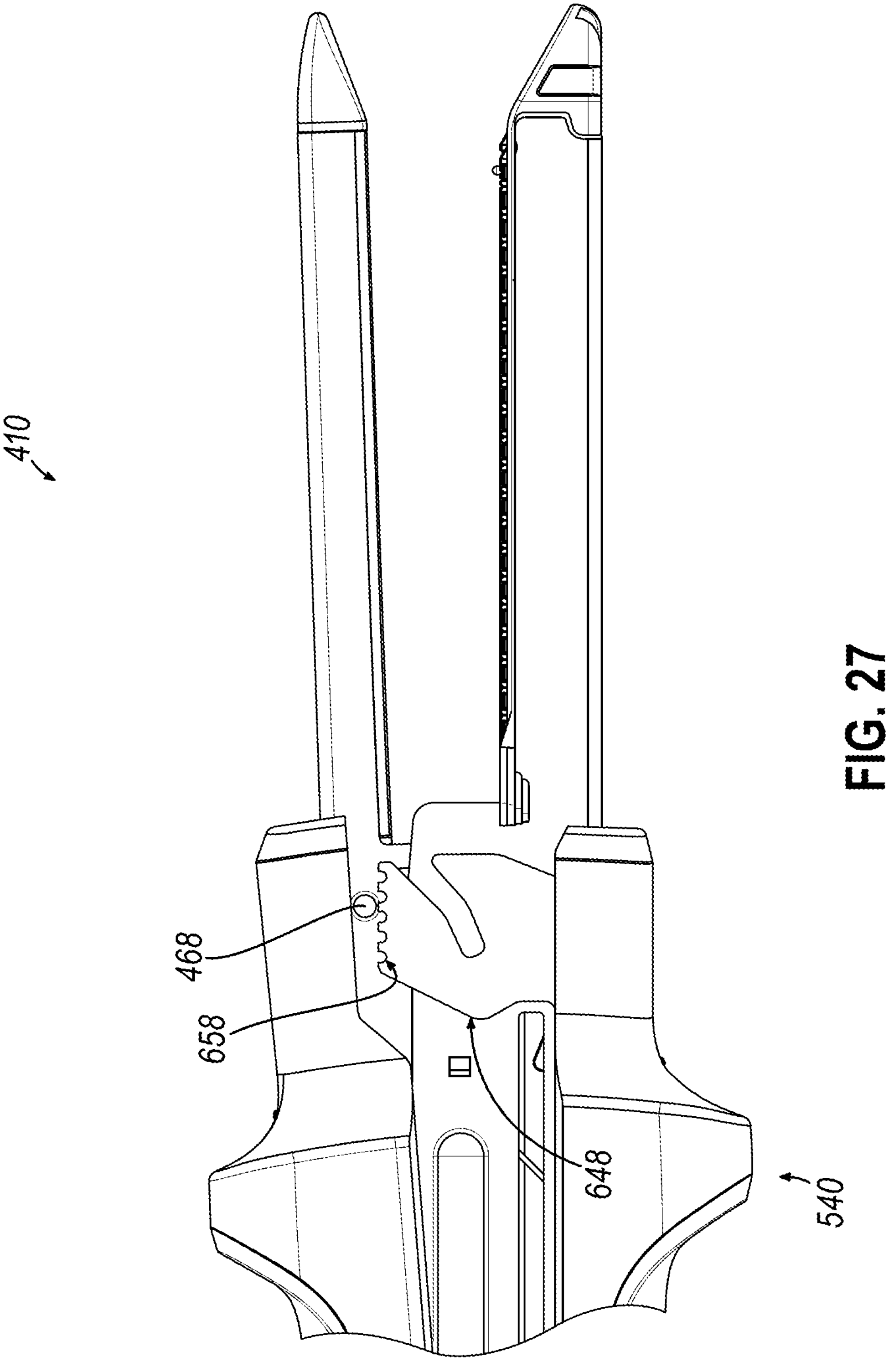
FIG. 27 depicts a side elevational view of a fourth illustrative linear surgical stapler, showing the clamp lever in a fully closed, non-latched position.

FIG. 27 shows an alternative respective jaw (648) of clamp lever (540). Respective jaw (648) may be substantially similar to respective jaw (548) but with the following differences. Jaw (648) may include a second latch pin engage feature in the form of a series of teeth (658) arranged longitudinally along an upper side of jaw (648). By way of example only, jaw (648) may include at least three teeth (658) in the series of teeth (658). The series of teeth (658) may collectively define a sawtooth profile and a corresponding recess between each tooth of the series of teeth (658). Each recess may be sized the same or smaller than latch pin (468). Latch pin (468) may skip or undulate across the surface of each tooth (658) during a misaligned rotation of clamp lever (540) to thus provide tactile feedback to operator that clamp lever (540) is not properly clamped.

Figure 28:
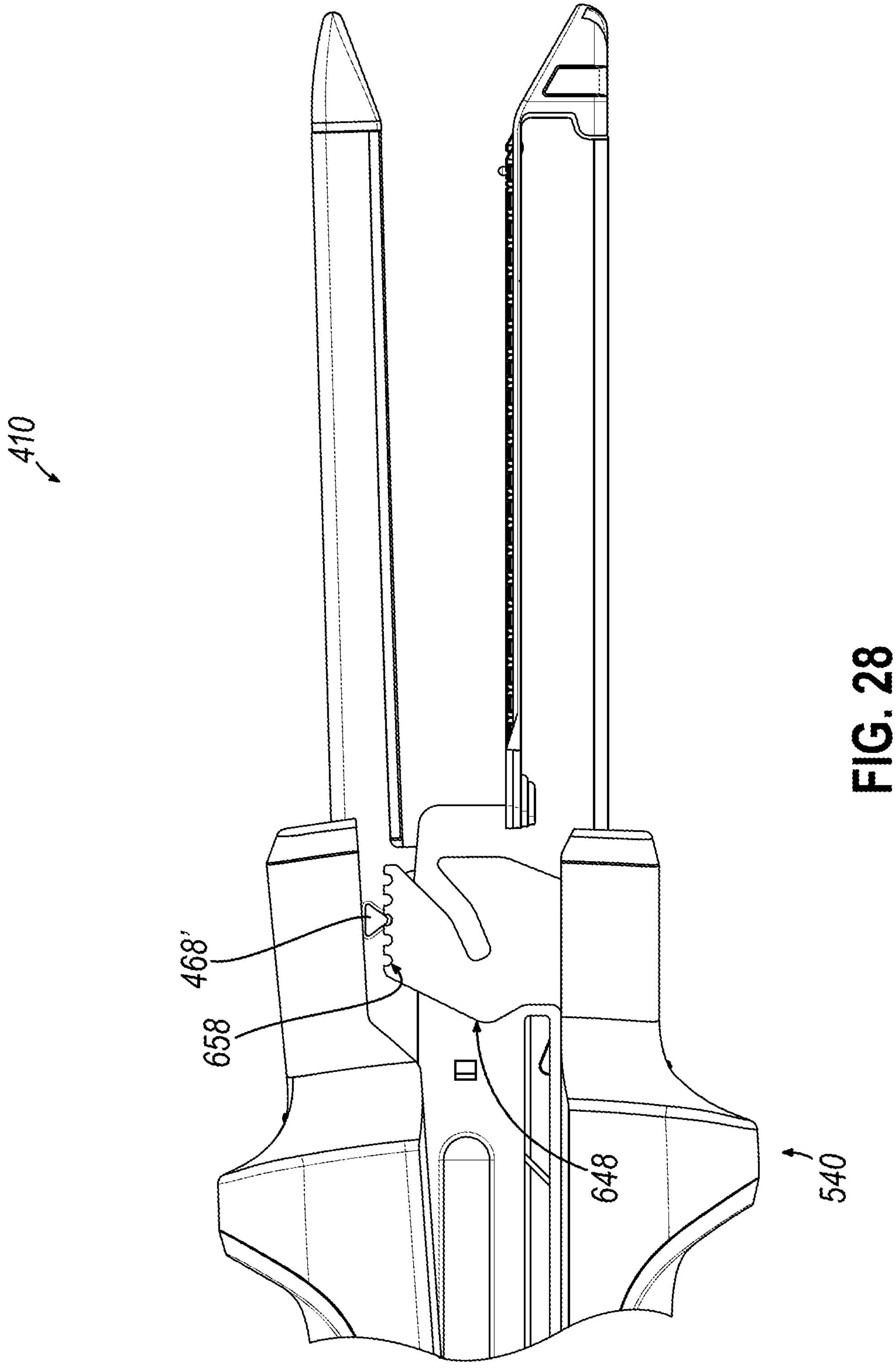
FIG. 28 depicts a side elevational view of a fifth illustrative linear surgical stapler, showing the clamp lever in a fully closed, non-latched position.

FIG. 28 depicts an alternative version of the stapler (410) of FIG. 27 but with a triangular latch pin (468') rather than circular latch pin (468). When compared to circular latch pin (458), triangular latch pin (468') may provide greater amplitude or sharper undulation during a misaligned rotation of clamp lever (540) to thus provide greater tactile feedback to the operator. For instance, a lower apex of the triangular profile of latch pin (468') may be configured to seat within the recesses positioned between teeth (658) and thereby provide a ratchet-type engagement between latch pin (468') and teeth (658) when latch pin (468') is misaligned with jaw slot (450).

G. Pin Securement to Anvil Channel Side Flanges

With respect to anvil half (14) described above, anvil latch pin (68) and proximal pin (70) may be secured to anvil channel (60) and anvil shroud (78) with a press fit. In some instances, it may be desirable to employ alternative methods and features for securing one or both of pins (68, 70) relative to anvil channel and/or anvil shroud (78). Illustrative examples of such configurations are shown and described below in connection with FIGS. 29-33B.

Figure 29:
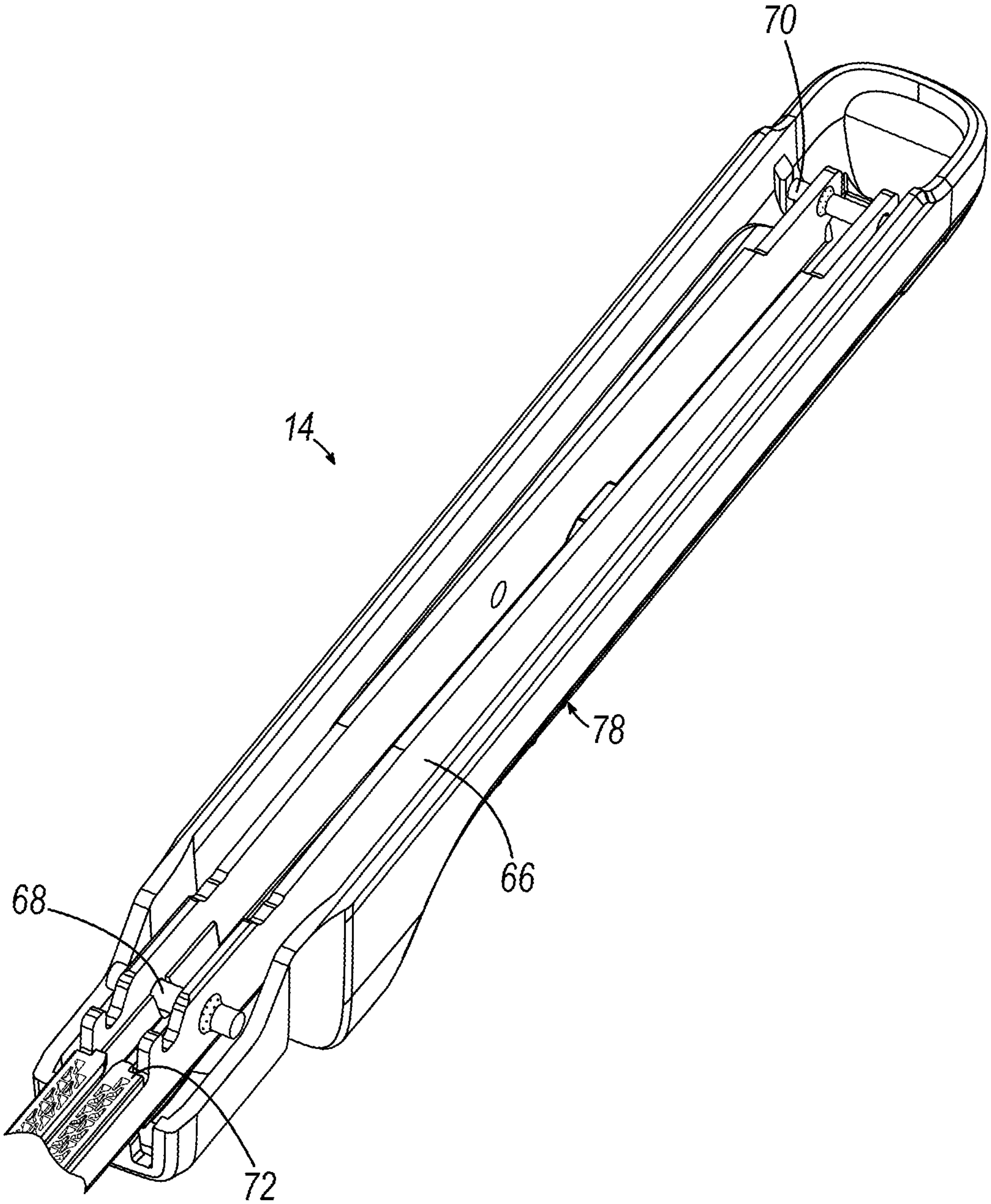
FIG. 29 depicts a perspective view of an anvil half of another illustrative linear surgical stapler, showing two welded pins of the anvil half.

FIG. 29 depicts anvil half (14) of FIG. 2 having latch pin (68) and proximal pin (70) welded to anvil channel side flanges (66). Latch pin (68) may be welded on lateral sides of anvil channel side flanges (66) (as shown) to thus allow an appropriate clearance for latch pin (68) to capture anvil plate (72) between anvil channel side flanges (66). Proximal pin (70) may be welded on the inside or medial sides of anvil channel side flanges (66) to thus provide clearance for anvil (12) to secure to proximal pin (70) between anvil channel side flanges (66) and anvil shroud (78). Anvil shroud (78) may be snap fitted onto latch pin (68) and proximal pin (70).

H. Anvil Shroud Securement to Anvil Channel

Figure 30A:
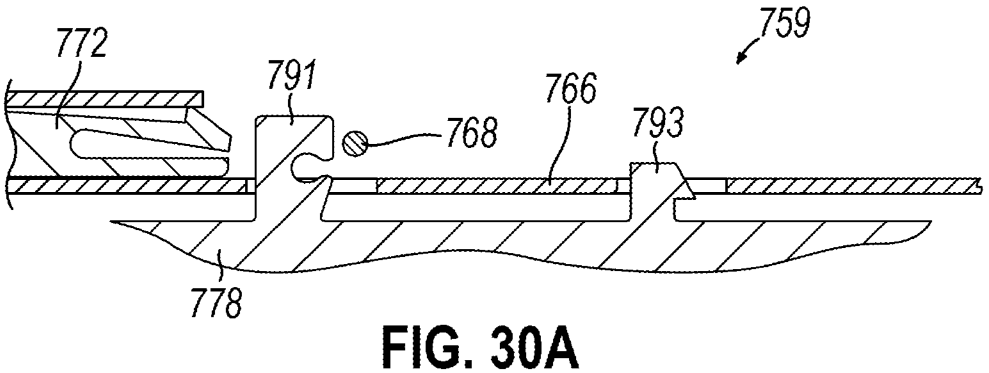
FIG. 30A depicts an enlarged side cross-sectional view of the anvil half of FIG. 29, showing select portions of an anvil shroud and a distal tip member of the anvil half in respective first longitudinal positions during assembly of the anvil half.
Figure 30B:
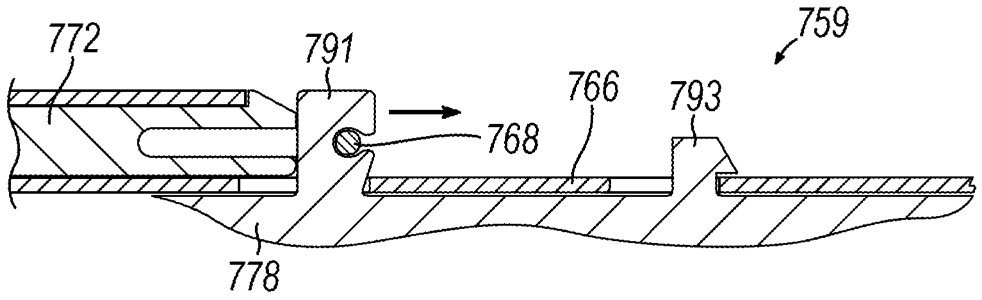
FIG. 30B depicts another enlarged side cross-sectional view of the anvil half of FIG. 29, showing each of the anvil shroud and the distal tip member in respective second longitudinal positions that constrain the components of the anvil half relative to one another during assembly of the anvil half.

FIGS. 30A-30B depict a first configuration (759) and method thereof for securing anvil shroud (778) to an anvil channel (766) with a latch pin (768). As shown in FIG. 30A, anvil shroud (778) may include a distal locking tab (791) and a proximal locking tab (793). Each locking tab (791, 793) may be configured to protrude through an opening in a floor of anvil channel (766) and be shifted proximally to lock distal locking tab (791) onto latch pin (768), as shown in FIG. 30B. A proximal end of distal tip member (772) having a cantilevered lock arm may then be proximally translated towards distal locking tab (791). The cantilevered lock arm may be biased to thus lock onto an anvil plate opposed from anvil channel floor (766) to prevent distal motion relative to anvil channel (766). Once locked, distal tip member (722)

may abut distal locking tab (791) of anvil shroud (778) to prevent distal locking tab (791) from unlocking from latch pin (768).

Figure 31A:
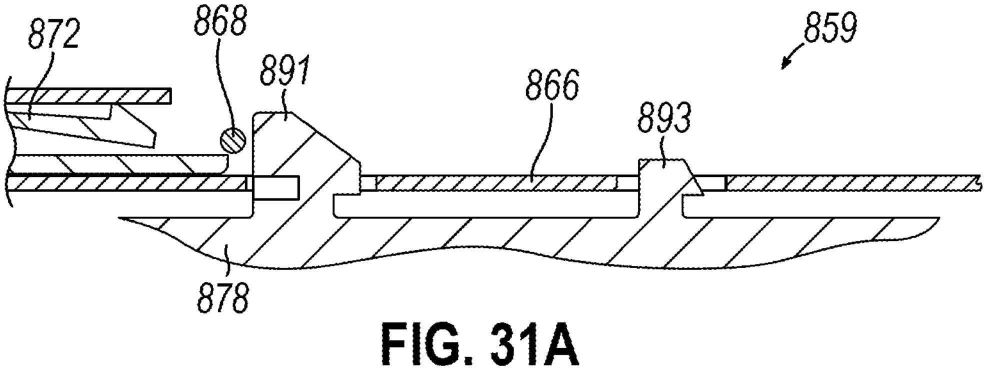
FIG. 31A depicts an enlarged side cross-sectional view of another illustrative variation of the anvil half of FIG. 29, showing select portions of an anvil shroud and a distal tip member of the anvil half in respective first longitudinal positions during assembly of the anvil half.
Figure 31B:
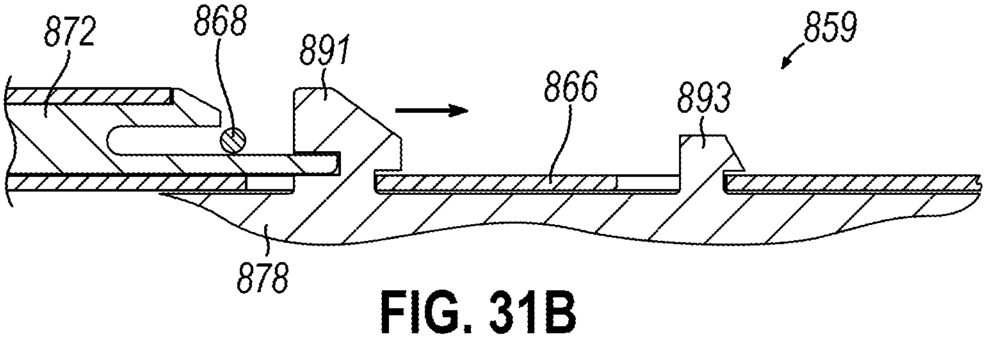
FIG. 31B depicts another enlarged side cross-sectional view of the anvil half of FIG. 31B, showing each of the anvil shroud and the distal tip member in respective second longitudinal positions that constrain the components of the anvil half relative to one another during assembly of the anvil half.

FIGS. 31A-31B depict a second configuration (859) and method thereof for securing anvil shroud (878) to an anvil channel (866) with a latch pin (868). As shown in FIG. 31A, anvil shroud (878) may include a distal locking tab (891) and a proximal locking tab (893). Each locking tab (891, 893) may be configured to protrude through an opening in a floor of anvil channel (866) and be shifted proximally for a partial capture onto the floor of anvil channel (866), as shown in FIG. 31B. Distal tip member (872) having a cantilevered lock arm may then be proximally translated towards distal locking tab (891). The cantilevered lock arm may be biased to thus lock onto an anvil plate opposed from the floor of anvil channel (866) to prevent distal motion relative to anvil channel (866). Once locked, a lower arm of distal tip member (822) may abut distal locking tab (891) of anvil shroud (878) to prevent distal locking tab (891) from unlocking from anvil channel side flange (866).

I. Alternative Pin Securement to Anvil Shroud

Figure 32:
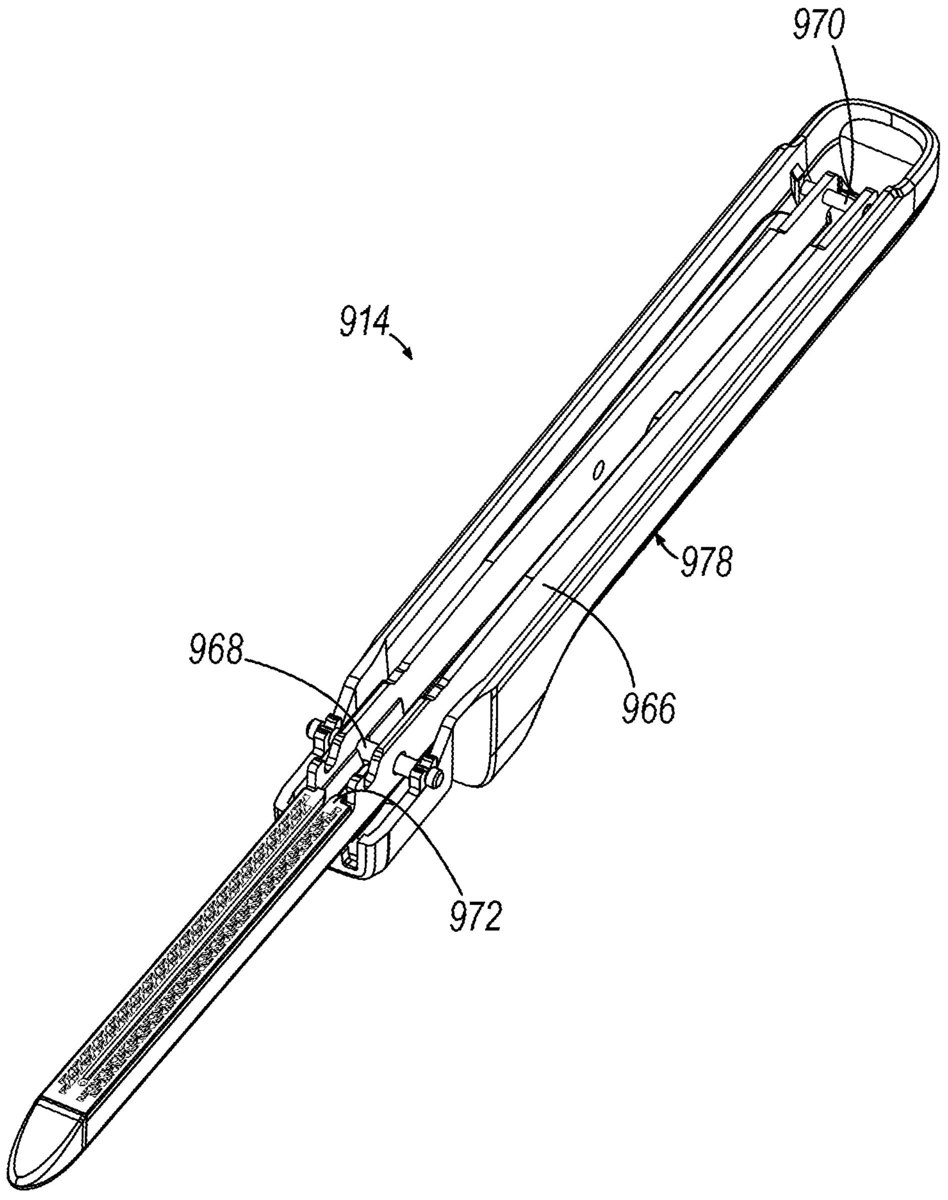
FIG. 32 depicts a perspective view of another an illustrative anvil half of a linear surgical stapler.
Figure 33A:
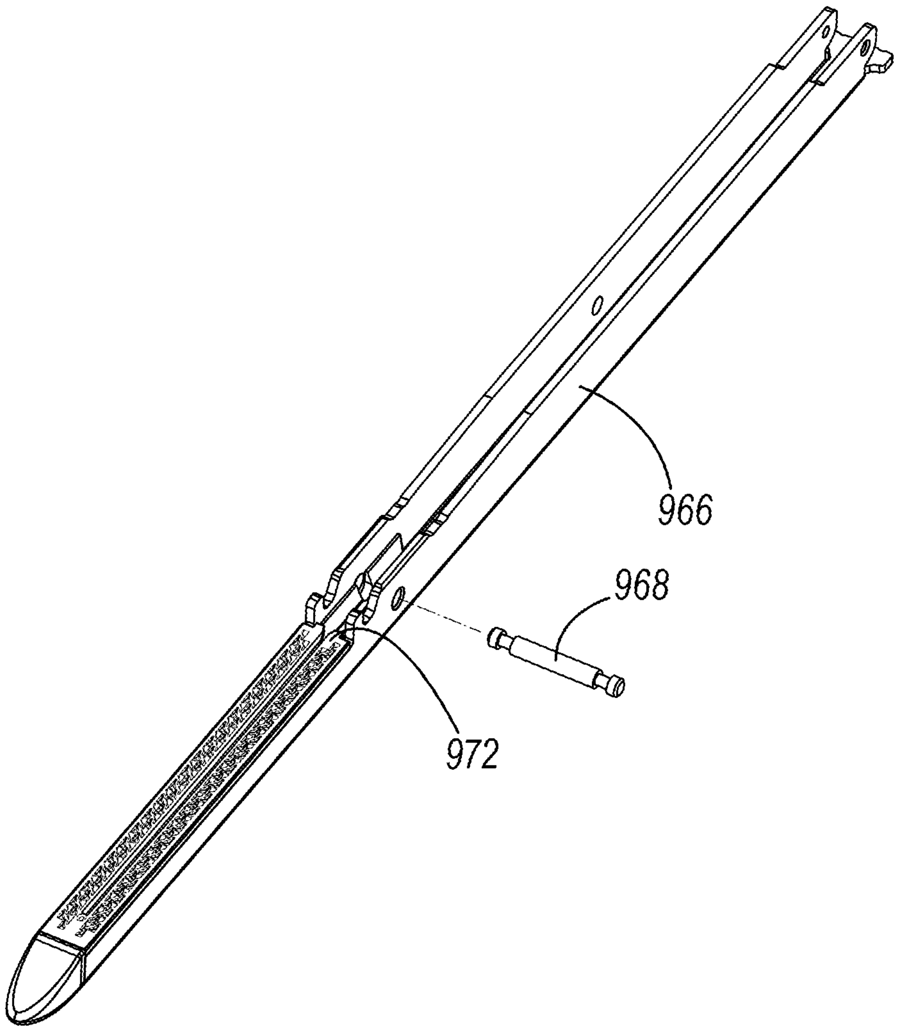
FIG. 33A depicts a perspective view of an anvil channel and a grooved latch pin of the anvil half of FIG. 32, showing the grooved latch pin being assembled with the anvil channel.
Figure 33B:
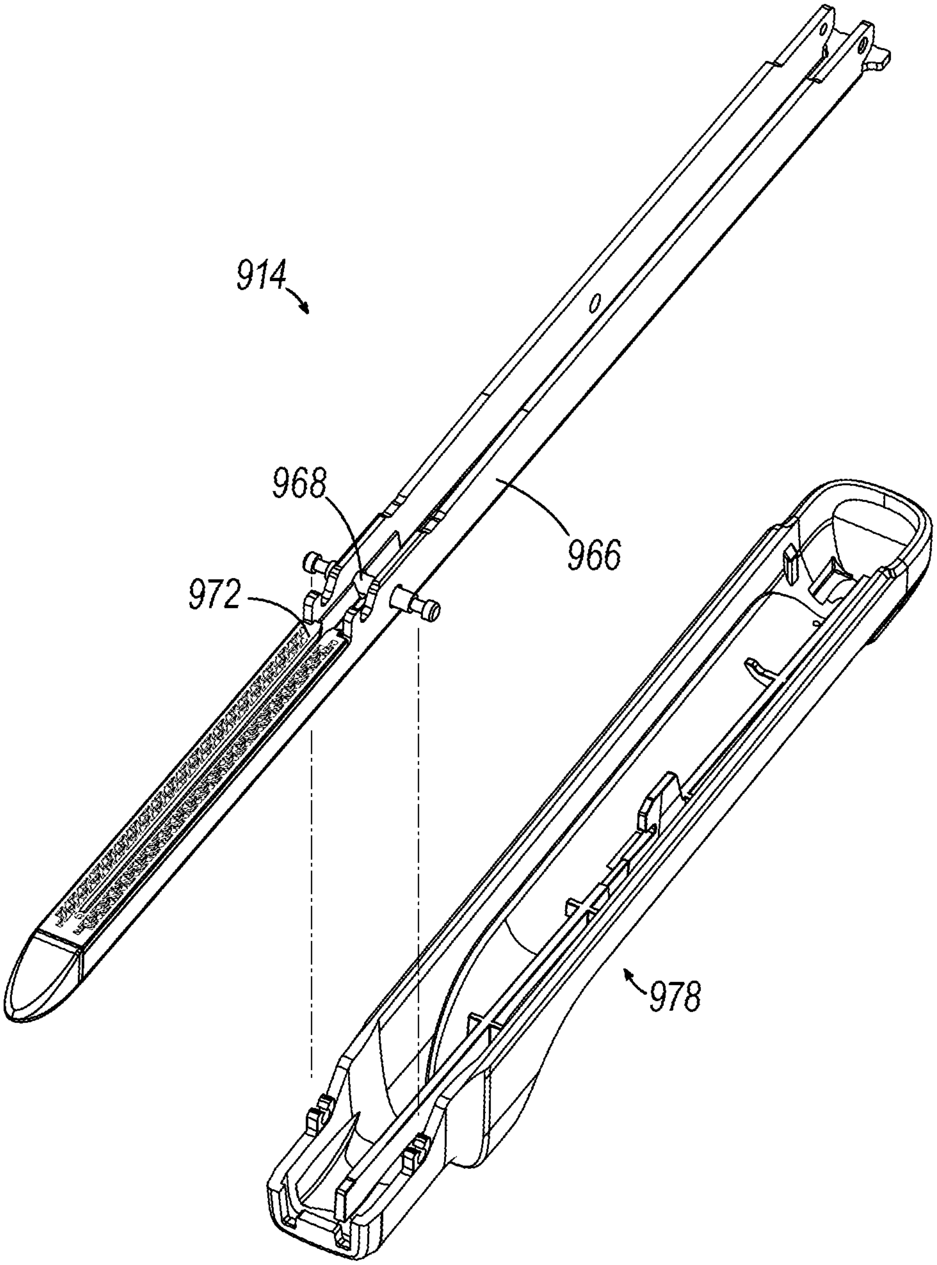
FIG. 33B depicts a disassembled perspective view of the anvil half of FIG. 32, showing the assembled anvil channel and grooved latch pin of FIG. 33A being aligned with corresponding features of an anvil shroud for assembly.

FIGS. 32-33B depict an alternative anvil half (914) having a latch pin (968) coupled to snap features of an anvil shroud (978) with a snap-fit engagement. As shown in FIGS. 33A and 33B, latch pin (968) may include annular grooves that are configured to be positioned laterally beyond side flanges of anvil channel (966) to thus allow anvil shroud (978) to snap onto latch pin (968) via the annular grooves. Once snapped, anvil shroud (978) may then laterally constrain latch pin (968) relative to anvil channel (966). Latch pin (968) may protrude laterally beyond anvil shroud (978) and may also be used to longitudinally constrain distal tip member (972) relative to anvil channel (966) as shown in FIG. 33B.

Additionally, in any of illustrative configurations shown and described above, the latch pin of an anvil half may be further constrained laterally relative to the respective anvil channel and anvil shroud by one or more retaining clips, such as an E-clip.

II. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprises: (a) a first elongate member having a distal portion configured to present a first stapling surface; (b) a second elongate member having a distal portion configured to present a second stapling surface, wherein the first and second elongate members are configured to releasably couple together to enable the first and second stapling surfaces to cooperate to clamp and staple tissue with a plurality of staples; (c) a clamp member, wherein the clamp member is movable relative to the first and second elongate members from a first position to a second position to approximate the first and second stapling surfaces for clamping tissue; (d) a latch member configured to transition from an unlatched state to a latched state to releasably retain the clamp member in the second position; and (e) a firing assembly, wherein the firing assembly is actuatable from a home position to fire the staples into the clamped tissue, wherein the latch member is configured to transition from the unlatched state to the latched state when the clamp member is in the second position while the firing assembly is in the home position, wherein the latch member is inhibited from transitioning from the unlatched state to the latched state when the clamp member is in the second position while the firing assembly is displaced from the home position.

Example 2

The apparatus of Example 1, wherein the first engagement feature comprises a slot having an open distal end and a closed proximal end, wherein the second engagement feature is configured to releasably capture the latch projection when the latch projection is misaligned with the slot and thereby inhibit the clamp member from assuming the second position.

Example 3

The apparatus of Example 2, wherein the second engagement feature includes a semi-circular profile configured to contact the latch projection.

Example 4

The apparatus of any of the preceding Examples, wherein the recess of the second engagement feature opens away from the other of the first elongate member or the second elongate member.

Example 5

The apparatus of any of the preceding Examples, wherein the clamp member includes a lever portion and a distal jaw portion, wherein the first and second engagement features are defined by the distal jaw portion, wherein the first engagement feature is positioned between the second engagement feature and the lever portion.

Example 6

The apparatus of Example 5, wherein the second engagement feature is positioned along an upper side of the distal jaw portion.

Example 7

The apparatus of any of the preceding Examples, wherein the first engagement feature is configured to engage the latch projection when the clamp member is oriented at an a first angle relative to a proximal end of the one of the first elongate member or the second elongate member, wherein the second engagement feature is configured to engage the latch projection when the clamp member is oriented at a second angle less than the angle relative to the proximal end of the one of the first elongate member or the second elongate member, wherein the second angle is less than the first angle.

Example 8

The apparatus of any of the preceding Examples, wherein the second engagement feature is configured to capture the latch projection and thereby inhibit the clamp member from advancing to the second position such that the first stapling surface is inhibited from approximating further towards the second stapling surface and is spaced apart from the second stapling surface by a gap distance.

Example 9

The apparatus of Example 8, wherein the second engagement feature is further configured to release the latch projection when the clamp member is returned to the first position so that the first stapling surface and the second stapling surface are farther spaced apart from one another by a distance greater than the gap distance.

Example 10

The apparatus of any of the preceding Examples, wherein the clamp member is configured to confront the other of the first elongate member or the second elongate member while the latch projection is captured by the second engagement feature.

Example 11

The apparatus of any of the preceding Examples, wherein the recess is defined by a first tooth, wherein the second engagement feature further defines a second tooth, wherein the first and second teeth are configured to frictionally engage the latch projection to provide a tactile indication to the operator.

Example 12

The apparatus of Example 11, wherein the second engagement feature further defines a third tooth, wherein the first, second, and third teeth collectively define a sawtooth profile.

Example 13

The apparatus of any of the preceding Examples, wherein the latch projection comprises a pin that extends laterally relative to a longitudinal axis of the one of the first elongate member or the second elongate member.

Example 14

The apparatus of Example 13, wherein the first engagement feature comprises a curved slot having an open distal end and a closed proximal end, wherein when the pin is properly aligned with the curved slot the pin is configured to advance proximally through the open distal end to the closed proximal end as the clamp member is rotated from the first position to the second position, wherein when the pin is misaligned with the curved slot the pin is configured to engage the second engagement feature as the clamp member is rotated from the first position toward the second position.

Example 15

The apparatus of Example 14, wherein the first and second stapling surfaces are configured to define a first gap distance therebetween when the pin is aligned with and captured by the curved slot, wherein the first and second stapling surfaces are configured to define a second gap distance therebetween when the latch pin is misaligned with the curved slot and is instead engaged by the second engagement feature, wherein the second gap distance is greater than the first gap distance by a gap difference observable by the operator, wherein the indication comprises the presence of the gap difference.

Example 16

The apparatus of any of the preceding Examples, wherein the first stapling surface comprises a deck having a plurality of openings that house a plurality of staples, wherein the second stapling surface comprises an anvil surface having a plurality of pockets configured to the form the staples when the apparatus is fired, wherein the clamp member is pivotably coupled with the first elongate member and the latch projection is coupled with the second elongate member, wherein the first position of the clamp member comprises an open position and the second position comprises a closed position the first and second stapling surfaces are configured to separate in order to transition the latch projection from the recess of the second engagement feature to the first engagement feature.

Example 17

An apparatus comprising: (a) a first elongate member having a latch projection and a distal portion configured to present a first stapling surface; (b) a second elongate member having a distal portion configured to present a second stapling surface, wherein the first and second elongate members are configured to hingedly couple together to enable the first and second stapling surfaces to cooperate to clamp and staple tissue with a plurality of staples; and (c) a clamp member pivotally coupled to one of the first elongate member or the second elongate member, wherein the clamp member includes: (i) a slot configured to releasably capture the latch projection while the clamp member advances from a first position to a second position to thereby approximate the first and second stapling surfaces for clamping tissue, and (ii) an engagement feature offset from the slot and comprising a recess, wherein the engagement feature is configured to engage the latch projection when the latch projection is misaligned with the slot to thereby provide an indication to an operator that the latch projection is misaligned with the slot.

Example 18

The apparatus of Example 17, wherein the recess is configured to releasably capture the latch projection when the latch projection is misaligned with the slot.

Example 19

The apparatus of any of Examples 17 through 18, wherein the engagement feature is configured to engage the latch projection so as to inhibit rotation of the clamp member into the second position.

Example 20

An apparatus comprising: (a) a first elongate member having a distal portion configured to present a first stapling surface; (b) a second elongate member having a distal portion configured to present a second stapling surface, wherein the first and second elongate members are configured to transition between an unclamped configuration in which the first and second stapling surfaces and spaced apart from one another, and a clamped configuration in which the first and second stapling surfaces confront one another, wherein the first and second stapling surfaces in the clamped configuration are configured to clamp and staple tissue with a plurality of staples (c) a latch projection presented by one of the first elongate member or the second elongate member; and (d) a third elongate member pivotally coupled to one of the first elongate member or the second elongate member, wherein the third elongate member includes a first opening configured to releasably capture the latch projection to provide the apparatus in the clamped configuration, and a second opening spaced apart from the first opening and configured to releasably capture the latch projection when the latch projection is misaligned with the first opening to thereby provide a visible and tactile indication to a user that the apparatus is not in the clamped configuration.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more teachings disclosed herein may be combined with any one or more teachings disclosed in U.S. Pat. No. 10,631,866, entitled "Release Mechanism for Linear Surgical Stapler," issued Apr. 28, 2020; U.S. Pat. No. 10,667,818, entitled "Lockout Assembly for Linear Surgical Stapler," issued Jun. 2, 2020; U.S. Pat. No. 10,932,781, entitled "Features to Align and Close Linear Surgical Stapler," issued Mar. 2, 2021; U.S. Pat. No. 10,898,197, entitled "Releasable Coupling Features for Proximal Portions of Linear Surgical Stapler," issued Jan. 26, 2021; U.S. Pat. No. 10,874,398, entitled "Firing Lever Assembly for Linear Surgical Stapler," issued Dec. 29, 2020; U.S. Pat. No. 10,687,819, entitled "Clamping Mechanism for Linear Surgical Stapler," issued Jun. 23, 2020; U.S. Pat. No. 10,898, 187, entitled "Firing System for Linear Surgical Stapler," issued Jan. 26, 2021; U.S. Pat. No. 11,033,266, entitled "Decoupling Mechanism for Linear Surgical Stapler, issued Jun. 15, 2021; U.S. Pat. No. 11,045,193, entitled "Anvil Assembly for Linear Surgical Stapler," issued Jun. 29, 2021; U.S. Pat. No. 10,905,419, entitled "Closure Assembly for Linear Surgical Stapler," issued Feb. 2, 2021; U.S. Pat. No. 11,278,285, entitled "Clamping Assembly for Linear Surgical Stapler," issued Mar. 22, 2022; U.S. Pat. No. 11,229,433, entitled "Linear Surgical Stapler," issued Jan. 25, 2022; U.S. Pub. No. 2022/0142641, entitled "System and Method for Forming Pockets in Anvil of Surgical Stapler," published May 12, 2022 and issued as U.S. Pat. No. 12,016,555 on Jun. 25, 2024; U.S. Pat. No. 11,224,425, entitled "Surgical Linear Cutter Wishbone Separation Mechanism with Detent," issued Jan. 18, 2022; U.S. Pat. No. 11,219,454, entitled "Pin Trap Mechanism for Surgical Linear Cutter," issued Jan. 11, 2022; U.S. Pub. No. 2021/0369272, entitled "Separation Mechanism for Surgical Linear Cutter," published Dec. 2, 2021 and issued as U.S. Pat. No. 11,399,827 on Aug. 2, 2022; U.S. patent application Ser. No. 17/489,879, entitled "Lockout Feature for Linear Surgical Stapler Cartridge," filed Sep. 30, 2021, issued as U.S. Pat. No. 11,937,812 on Mar. 26, 2024; U.S. patent application Ser. No. 29/842,580, entitled "Staple Cartridge for Linear Surgical Stapler," filed Jun. 16, 2022, issued as U.S. Pat. No. D1,067,431 on Mar. 18, 2025; and/or U.S. patent application Ser. No. 29/842, 581, entitled "Linear Surgical Stapler," filed Jun. 16, 2022. The disclosure of each of these references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Intuitive Surgical, Inc., of Sunnyvale, California or by Auris Health of Redwood City, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:

(a) a first elongate body having a distal portion configured to present a first stapling surface;

(b) a second elongate body having a distal portion configured to present a second stapling surface, wherein the first and second elongate bodies are configured to releasably couple together to enable the first and second stapling surfaces to cooperate to clamp and staple tissue with a plurality of staples;

(c) a latch projection extending from one of the first elongate body or the second elongate body; and (d) a clamp movably coupled with the other of the first elongate body or the second elongate body, wherein the clamp includes:

(i) a first engagement portion configured to releasably capture the latch projection while the clamp advances from a first position to a second position to thereby approximate the first and second stapling surfaces for clamping tissue, and (ii) a second engagement portion offset from the first engagement portion and comprising a recess, wherein the second engagement portion is configured to engage the latch projection when the latch projection is misaligned with the first engagement portion to thereby provide an indication to an operator that the latch projection is misaligned with the first engagement portion.

2. The apparatus of claim 1, wherein the first engagement portion comprises a slot having an open distal end and a closed proximal end, wherein the second engagement portion is configured to releasably capture the latch projection when the latch projection is misaligned with the slot and thereby inhibit the clamp from assuming the second position.

3. The apparatus of claim 2, wherein the second engagement portion includes a semi-circular profile configured to contact the latch projection.

4. The apparatus of claim 1, wherein the recess of the second engagement portion opens away from the other of the first elongate body or the second elongate body.

5. The apparatus of claim 1, wherein the clamp includes a lever portion and a distal jaw portion, wherein the first and second engagement portions are defined by the distal jaw portion, wherein the first engagement portion is positioned between the second engagement feature portion and the lever portion.

6. The apparatus of claim 5, wherein the second engagement portion is positioned along an upper side of the distal jaw portion.

7. The apparatus of claim 1, wherein the first engagement portion is configured to engage the latch projection when the clamp is oriented at a first angle relative to a proximal end of the one of the first elongate body or the second elongate body, wherein the second engagement portion is configured to engage the latch projection when the clamp is oriented at a second angle relative to the proximal end of the one of the first elongate body or the second elongate body, wherein the second angle is less than the first angle.

8. The apparatus of claim 1, wherein the second engagement portion is configured to capture the latch projection and thereby inhibit the clamp from advancing to the second position such that the first stapling surface is inhibited from approximating further towards the second stapling surface and is spaced apart from the second stapling surface by a gap distance.

9. The apparatus of claim 8, wherein the second engagement portion is further configured to release the latch projection when the clamp is returned to the first position so that the first stapling surface and the second stapling surface are spaced apart from one another by a distance greater than the gap distance.

10. The apparatus of claim 1, wherein the clamp is configured to confront the other of the first elongate body or the second elongate body while the latch projection is captured by the second engagement portion.

11. The apparatus of claim 1, wherein the recess is defined by a first tooth, wherein the second engagement portion further defines a second tooth, wherein the first and second teeth are configured to frictionally engage the latch projection to provide a tactile indication to the operator.

12. The apparatus of claim 11, wherein the second engagement portion further defines a third tooth, wherein the first, second, and third teeth collectively define a sawtooth profile.

13. The apparatus of claim 1, wherein the latch projection comprises a pin that extends laterally relative to a longitudinal axis of the one of the first elongate body or the second elongate body.

14. The apparatus of claim 13, wherein the first engagement portion comprises a curved slot having an open distal end and a closed proximal end, wherein when the pin is properly aligned with the curved slot the pin is configured to advance proximally through the open distal end to the closed proximal end as the clamp is rotated from the first position to the second position, wherein when the pin is misaligned with the curved slot the pin is configured to engage the second engagement portion as the clamp is rotated from the first position toward the second position.

15. The apparatus of claim 14, wherein the first and second stapling surfaces are configured to define a first gap distance therebetween when the pin is aligned with and captured by the curved slot, wherein the first and second stapling surfaces are configured to define a second gap distance therebetween when the latch pin is misaligned with the curved slot and is instead engaged by the second engagement portion, wherein the second gap distance is greater than the first gap distance by a gap difference observable by the operator, wherein the indication comprises the presence of the gap difference.

16. The apparatus of claim 1, wherein the first stapling surface comprises a deck having a plurality of openings that house a plurality of staples, wherein the second stapling surface comprises an anvil surface having a plurality of pockets configured to the form the staples when the apparatus is fired, wherein the clamp is pivotably coupled with the first elongate body and the latch projection is coupled with the second elongate body, wherein the first position of the clamp comprises an open position and the second position comprises a closed position.

17. An apparatus comprising:

(a) a first elongate body having a distal portion configured to present a first stapling surface;

(b) a second elongate body having a distal portion configured to present a second stapling surface, wherein the first and second elongate bodies are configured to releasably couple together to enable the first and second stapling surfaces to cooperate to clamp and staple tissue with a plurality of staples;

(c) a pin extending from one of the first elongate body or the second elongate body; and (d) a clamp movably coupled with the other of the first elongate body or the second elongate body, wherein the clamp includes:

(i) a first engagement opening sized to releasably capture the pin, and (ii) a second engagement opening offset from the first engagement opening and sized to releasably capture the pin, wherein the first engagement opening is configured to engage the pin when the pin is in a first position, wherein the second engagement opening is configured to engage the pin when the pin is in a second position, and wherein the first position and the second position are different.

18. The apparatus of claim 17, wherein the first position is distal to the second position.

19. The apparatus of claim 17, wherein the first and second stapling surfaces are configured to be further apart when the pin is in the second position than in the first position.

20. An apparatus comprising:

(a) a first elongate body having a distal portion configured to present a first stapling surface;

(b) a second elongate body having a distal portion configured to present a second stapling surface, wherein the second elongate body is configured to move from a first position to a second position relative to the first elongate body to thereby cooperate with the first elongate body to clamp and staple tissue with a plurality of staples;

(c) a latch projection extending from the second elongate body; and (d) a clamp movably coupled with the first elongate body, wherein the clamp includes:

(i) a first engagement portion configured to releasably capture the latch projection while the second elongate body advances from the first position to the second position to thereby approximate the first and second stapling surfaces for clamping tissue, and (ii) a second engagement portion offset from the first engagement portion and comprising a recess, wherein the second engagement portion is configured to engage the latch projection when the second elongate body is in the first position to thereby provide an indication to an operator that the latch projection is misaligned with the first engagement portion.

* * * * *